(12) United States Patent
Li

(10) Patent No.: US 11,478,535 B2
(45) Date of Patent: *Oct. 25, 2022

(54) METHOD FOR PREVENTING AND TREATING FATTY LIVER

(71) Applicant: Talengen International Limited, Wanchai (HK)

(72) Inventor: Jinan Li, Guangdong (CN)

(73) Assignee: Talengen International Limited, Hong Kong (CN)

( * ) Notice: Subject to any disclaimer, the term of this patent is extended or adjusted under 35 U.S.C. 154(b) by 162 days.

This patent is subject to a terminal disclaimer.

(21) Appl. No.: 16/469,618

(22) PCT Filed: Jun. 19, 2017

(86) PCT No.: PCT/CN2017/089047
§ 371 (c)(1),
(2) Date: Jun. 13, 2019

(87) PCT Pub. No.: WO2018/107688
PCT Pub. Date: Jun. 21, 2018

(65) Prior Publication Data
US 2020/0085920 A1 Mar. 19, 2020

(30) Foreign Application Priority Data

Dec. 15, 2016 (WO) ................ PCT/CN2016/110168
Dec. 15, 2016 (WO) ................ PCT/CN2016/110172

(51) Int. Cl.
| | | |
|---|---|---|
| *A61K 38/48* | (2006.01) | |
| *A61P 9/10* | (2006.01) | |
| *A61P 3/06* | (2006.01) | |
| *A61P 3/10* | (2006.01) | |
| *A61P 1/16* | (2006.01) | |
| *A61P 9/00* | (2006.01) | |
| *A61K 45/06* | (2006.01) | |

(52) U.S. Cl.
CPC .............. *A61K 38/484* (2013.01); *A61P 1/16* (2018.01); *A61P 3/06* (2018.01); *A61P 3/10* (2018.01); *A61P 9/00* (2018.01); *A61P 9/10* (2018.01); *A61K 45/06* (2013.01); *C12Y 304/21007* (2013.01)

(58) Field of Classification Search
CPC . A61K 38/484; A61P 1/16; A61P 9/00; A61P 3/06; A61P 3/10; C12Y 304/21007
See application file for complete search history.

(56) References Cited

U.S. PATENT DOCUMENTS

| | | |
|---|---|---|
| 4,245,051 A | 1/1981 | Reich |
| 4,774,338 A | 9/1988 | Priesnitz |
| 4,996,050 A | 2/1991 | Tsukada |
| 5,304,383 A | 4/1994 | Eibl et al. |
| 5,597,800 A | 1/1997 | Eibl et al. |
| 5,637,299 A | 6/1997 | Mcdonagh |
| 5,776,452 A | 7/1998 | Eibl |
| 7,056,943 B2 | 6/2006 | Elokdah |
| 7,067,492 B2* | 6/2006 | Ny .......................... A61P 17/02 514/9.4 |
| 8,318,661 B2 | 11/2012 | Ny et al. |
| 8,357,147 B2 | 1/2013 | Burkinshaw |
| 8,637,010 B2 | 1/2014 | Ny et al. |
| 8,679,482 B2 | 3/2014 | Ny et al. |
| 10,086,052 B2 | 10/2018 | Ny et al. |
| 10,709,771 B2 | 7/2020 | Li |
| 10,864,257 B2 | 12/2020 | Li |
| 2002/0103129 A1 | 8/2002 | Ge |
| 2002/0159992 A1 | 10/2002 | Henkin |
| 2003/0026798 A1 | 2/2003 | Zimmerman |
| 2003/0054988 A1 | 3/2003 | Ji |
| 2003/0147876 A1 | 8/2003 | Ni |
| 2004/0038891 A1 | 2/2004 | Bisgaier |
| 2004/0043026 A1 | 3/2004 | Tuan |
| 2004/0247564 A1 | 12/2004 | Itescu |
| 2005/0124036 A1 | 6/2005 | Susilo |
| 2008/0017694 A1 | 1/2008 | Schnell et al. |
| 2008/0200387 A1* | 8/2008 | Wu .......................... A61P 7/00 514/13.3 |
| 2009/0093442 A1 | 4/2009 | Lynch |
| 2009/0123582 A1 | 5/2009 | Kuwahara |
| 2009/0208448 A1 | 8/2009 | Solomon |

(Continued)

FOREIGN PATENT DOCUMENTS

| | | |
|---|---|---|
| CA | 2145841 A1 | 10/1995 |
| CA | 2475277 A1 | 8/2003 |

(Continued)

OTHER PUBLICATIONS

Harvard. What to do about nonalcoholic fatty liver disease. Harvard Health Publishing. 2012;1-4.*
UCSD. Nonalcoholic fatty liver disease. UC San Diego Health. 2021;1-2.*
Obesity. Fatty liver disease and your heart. Harvard Health Publishing. 2016;1-3.*
Bhatt et al. Fatty liver disease in diabetes mellitus. HepatoBiliary Surg Nutr. 2015;4(2):101-108.*

(Continued)

*Primary Examiner* — Lynn Y Fan
(74) *Attorney, Agent, or Firm* — Morrison & Foerster LLP

(57) ABSTRACT

The present invention relates to a method for preventing and/or treating fatty liver and its related conditions in a subject, comprising administering an effective amount of plasminogen to the subject; in another aspect, the present invention further relates to a medicament, a pharmaceutical composition, an article of manufacture, and a kit comprising plasminogen which are useful for preventing and/or treating fatty liver and its related conditions in the subject.

17 Claims, 10 Drawing Sheets

Specification includes a Sequence Listing.

(56) References Cited

U.S. PATENT DOCUMENTS

| | | |
|---|---|---|
| 2009/0239868 A1 | 9/2009 | Muto |
| 2009/0275513 A1 | 11/2009 | Rebbeor |
| 2010/0028321 A1 | 2/2010 | Ny et al. |
| 2010/0099600 A1 | 4/2010 | Ny |
| 2010/0184661 A1 | 7/2010 | Luo |
| 2011/0039766 A1 | 2/2011 | Szeto |
| 2011/0318812 A1 | 12/2011 | Hunt |
| 2012/0022080 A1 | 1/2012 | Miyata |
| 2012/0058537 A1 | 3/2012 | Mahboudi |
| 2012/0114630 A1 | 5/2012 | Zwaal |
| 2014/0121241 A1 | 5/2014 | Nakajima |
| 2014/0273275 A1 | 9/2014 | Jacobs |
| 2015/0224073 A1 | 8/2015 | Green |
| 2016/0184411 A1 | 6/2016 | Ny et al. |
| 2016/0200831 A1 | 7/2016 | Pritsker |
| 2018/0369345 A1 | 12/2018 | Li |
| 2019/0015485 A1 | 1/2019 | Li |
| 2019/0083586 A1 | 3/2019 | Li |
| 2019/0151421 A1 | 5/2019 | Li et al. |
| 2019/0231854 A1 | 8/2019 | Robitaille |
| 2019/0328850 A1 | 10/2019 | Li |

FOREIGN PATENT DOCUMENTS

| | | |
|---|---|---|
| CA | 2770688 A1 | 2/2011 |
| CA | 2823491 A1 | 7/2012 |
| CA | 2707266 A1 | 12/2013 |
| CA | 3002915 A1 | 5/2017 |
| CN | 1408431 A | 4/2003 |
| CN | 1451746 A | 10/2003 |
| CN | 1662548 A | 8/2005 |
| CN | 1668312 A | 9/2005 |
| CN | 1668645 | 9/2005 |
| CN | 1720051 A | 1/2006 |
| CN | 1726191 A | 1/2006 |
| CN | 1768138 A | 5/2006 |
| CN | 101015686 A | 8/2007 |
| CN | 101132788 A | 2/2008 |
| CN | 101563100 A | 10/2009 |
| CN | 101573134 A | 11/2009 |
| CN | 101628113 A | 1/2010 |
| CN | 101686994 A | 3/2010 |
| CN | 101842093 A | 9/2010 |
| CN | 101897925 A | 12/2010 |
| CN | 101918548 A | 12/2010 |
| CN | 102121023 A | 7/2011 |
| CN | 102123721 A | 7/2011 |
| CN | 102154253 A | 8/2011 |
| CN | 102188699 A | 9/2011 |
| CN | 102199587 A | 9/2011 |
| CN | 102378753 A | 3/2012 |
| CN | 102482338 A | 5/2012 |
| CN | 102532326 A | 7/2012 |
| CN | 102647994 A | 8/2012 |
| CN | 102660564 A | 9/2012 |
| CN | 103384722 A | 11/2013 |
| CN | 103656630 A | 3/2014 |
| CN | 103703140 A | 4/2014 |
| CN | 103764163 A | 4/2014 |
| CN | 104274449 A | 1/2015 |
| CN | 105008323 A | 10/2015 |
| CN | 105705520 A | 6/2016 |
| CN | 1856319 A | 11/2016 |
| EP | 0307847 A2 | 3/1989 |
| EP | 0192667 B1 | 10/1994 |
| EP | 0631786 A1 | 1/1995 |
| EP | 0674906 A2 | 10/1995 |
| EP | 1666469 A1 | 6/2006 |
| EP | 0200145 A2 | 12/2008 |
| EP | 2000145 A2 | 12/2008 |
| EP | 2201946 A1 | 6/2010 |
| EP | 3391901 A1 | 10/2018 |
| EP | 3391902 A1 | 10/2018 |
| EP | 3556387 A1 | 10/2019 |
| EP | 3556391 A1 | 10/2019 |

| | | | |
|---|---|---|---|
| JP | 32153224 A | 7/1987 | |
| JP | H07145076 A | 6/1995 | |
| JP | 2005507244 A | 3/2005 | |
| JP | 2005525798 A | 9/2005 | |
| JP | 2008534508 A | 8/2008 | |
| JP | 2010502600 A | 1/2010 | |
| JP | 2010515694 A | 5/2010 | |
| JP | 2012532596 A | 12/2012 | |
| JP | 2019500423 A | 1/2019 | |
| JP | 2019500424 A | 1/2019 | |
| JP | 2020502154 A | 1/2020 | |
| JP | 2020502156 A | 1/2020 | |
| JP | 2020511416 A | 4/2020 | |
| TW | 201722468 | 7/2017 | |
| TW | I624268 B | 5/2018 | |
| TW | 201822791 A | 7/2018 | |
| TW | 201822792 A | 7/2018 | |
| TW | 201822799 | 7/2018 | |
| TW | 201822805 A | 7/2018 | |
| TW | 201822806 A | 7/2018 | |
| TW | 201822809 A | 7/2018 | |
| TW | 201822810 A | 7/2018 | |
| TW | 201822812 A | 7/2018 | |
| TW | 201829448 A | 8/2018 | |
| TW | 200908973 A | 3/2019 | |
| WO | 199401128 A1 | 1/1994 | |
| WO | 199512407 A1 | 5/1995 | |
| WO | 199900420 A1 | 1/1999 | |
| WO | WO200048595 A1 | 8/2000 | |
| WO | WO200049871 A1 | 8/2000 | |
| WO | 200240510 A2 | 5/2002 | |
| WO | 2003014145 A2 | 2/2003 | |
| WO | 2003033019 A2 | 4/2003 | |
| WO | 200240510 A3 | 6/2003 | |
| WO | 2003033019 A3 | 7/2003 | |
| WO | 2003066842 A2 | 8/2003 | |
| WO | 2003014145 A3 | 12/2003 | |
| WO | 2003066842 A3 | 6/2004 | |
| WO | 2006095713 A1 | 9/2006 | |
| WO | 2006102395 A2 | 9/2006 | |
| WO | 2006122249 A2 | 11/2006 | |
| WO | 2006102395 A3 | 5/2007 | |
| WO | 2006122249 A3 | 6/2007 | |
| WO | WO2008026999 A2 | 3/2008 | |
| WO | WO2008027000 A2 | 3/2008 | |
| WO | WO2009089059 A2 | 7/2009 | |
| WO | WO2010076655 A1 | 7/2010 | |
| WO | WO2010083570 A1 | 7/2010 | |
| WO | 2010125148 A2 | 11/2010 | |
| WO | 2010125148 A3 | 1/2011 | |
| WO | WO2011004011 A1 | 1/2011 | |
| WO | 2011139973 A2 | 11/2011 | |
| WO | 2011139973 A3 | 3/2012 | |
| WO | WO2012135729 A2 | 10/2012 | |
| WO | WO2013024074 A1 | 2/2013 | |
| WO | WO-2013024074 A1 * | 2/2013 | ............ A61K 38/48 |
| WO | WO2014070983 A1 | 5/2014 | |
| WO | 2015023752 A1 | 2/2015 | |
| WO | 2015026494 A2 | 2/2015 | |
| WO | 2015026494 A3 | 11/2015 | |
| WO | 2017077380 A1 | 5/2017 | |
| WO | WO2017101869 A1 | 6/2017 | |
| WO | WO2018107684 A1 | 6/2018 | |
| WO | WO2018107685 A1 | 6/2018 | |
| WO | WO2018107688 A1 | 6/2018 | |
| WO | WO2018107692 A1 | 6/2018 | |
| WO | WO2018107707 A1 | 6/2018 | |
| WO | WO2018108161 A1 | 6/2018 | |
| WO | 2018234861 A1 | 12/2018 | |

OTHER PUBLICATIONS

Ogbru et al. Type 2 oral diabetes medications (Oral). MedicineNet. 2016;1-4.*

Corvera et al. Adipose Tissue Angiogenesis: Impact on Obesity and Type-2 Diabetes. Biochim Biophys Acta. 2014;1842(3):463-472.*

Qureshi et al. Metabolic liver disease of obesity and role of adipose tissue in the pathogenesis of nonalcoholic fatty liver disease. WJG. 2007;13(26):3540-3553.*

(56) References Cited

OTHER PUBLICATIONS

Alessi, M. C. et al. (Aug. 24, 2006). "PAI-1 and the Metabolic Syndrome: Links, Causes, and Consequences," Arterioscler Thromb Vasc Biol. 26(10):2200-2207.
Beier, J.I. et al. (Jan. 31, 2012). "Alcoholic Liver Disease and the Potential Role of Plasminogen Activator Inhibitor-1 and Fibrin Metabolism," Exp. Biol. Med. 237(1):1-9, 19 pages.
Brouwers, M.C.G.J. et al. (2008, e-pub. Feb. 8, 2008). "Plasma PAI-1 Levels are Independently Related to Fatty Liver and Hypertriglyceridemia in Familial Combined Hyperlipidemia, Involvement of Apolipoprotein E," Thrombosis Research 122:466-472.
Chang, M.L. et al. (Dec. 31, 2015). "Plasminogen Activator Inhibitor-1 is Independently Associated With Non-Alcoholic Fatty Liver Disease Whereas Leptin and Adipo-Nectin Vary Between Genders," Journal of Gastroenterology and Hepatology, 30:329-336.
Chen, W. et al. (Sep. 30, 2009). "Effects of Fibrate on the Pathophysiology of Kidney," International Journal of Endocrinology and Metabolism 29(5):332-334. English Abstract.
Crandall, D. L. et al. (Oct. 20006, e-pub. Jul. 6, 2006). "Modulation of Adipose Tissue Development by Pharmacological Inhibition of PAI-1," Arterioscler Thromb Vasc Biol. 26(10):2209-2215.
Darvall, K. A. L. et al. (Dec. 20, 2006). "Obesity and Thrombosis," European Journal of Vascular and Endovascular Surgery 33(2):223-233.
Deng, Y. et al. (Jan. 31, 2005). "Relationship Between Phlegmstasis Syndrome and Fibrinolytic Status in Patients with Non-alcoholic Fatty Liver," Chinese Journal of Integrated Traditional and Western Medicine pp. 22-24. English Abstract.
Forsgren, M. et al. (Mar. 19, 1999). "Plasminogen [*Homo sapiens*]," NCBI Reference Sequence: NP_000292, 4 pages.
International Search Report, dated Aug. 16, 2017, PCT Application No. PCT/CN2017/089047, 5 pages.
International Search Report, dated Aug. 25, 2017, PCT Application No. PCT/CN2017/089046, 6 pages.
International Search Report, dated Sep. 13, 2017, PCT Application No. PCT/CN2017/089052, 6 pages.
International Search Report, dated Sep. 15, 2017, PCT Application No. PCT/CN2017/089051, 6 pages.
International Search Report, dated Sep. 20, 2017, PCT Application No. PCT/CN2017/089048, 5 pages.
International Search Report, dated Sep. 6, 2017, PCT Application No. PCT/CN2017/089049, 6 pages.
Joshi-Barve, S. et al. (Jul. 31, 2015). "Alcoholic, Nonalcoholic, and Toxicant-Associated Steatohepatitis: Mechanistic Similarities and Differences," CMGH 1:356-367.
Kaji, H. (Oct. 31, 2016). "Adipose Tissue-Derived Plasminogen Activator Inhibitor-1 Function and Regulation," Comprehensive Physiology 6:1873-1896.
Kurt, B. et al. (Mar. 3, 2015). "Lipoprotein(a): Clinical Aspects and Future Challenges," Clin. Res. Cardiol. 10 (Suppl.):26-32.
Liu, J.Y. (2014, e-pub. Oct. 28, 2014). "Ethanol and Liver: Recent Insights Into the Mechanisms of Ethanol-Induced Fatty Liver," World J. Gastroenterol, 20(40):14672-14685.
Ma, L.-J. et al. (Feb. 2004). "Prevention of Obesity and Insulin Resistance in Mice Lacking Plasminogen Activator Inhibitor 1," Diabetes 53:336-346.
Rupnick, M.A. et al. (Aug. 6, 2002). "Adipose Tissue Mass Can be Regulated Through the Vasculature," PNAS 99(16):10730-10735.
Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.
Plow, E. F. et al. (Jul. 31, 2014)., "The Functions of Plasminogen in Cardiovascular Disease," Trends in Cardiovascular Medicine 14(5):180-186.
Restrepo, L. et al. (2009, e-pub. Aug. 22, 2009). "Impact of Hyperlipidemia and Statins on Ischemic Stroke Outcomes after Intra-Arterial Fibrinolysis and Percutaneous Mechanical Embolectomy," Cerebrovasc Dis. 28:384-390.

Shen, H. et al. (Apr. 28, 2009). "Roles of Adipocytokines in the Pathogenesis of Non-alcoholic Fatty Liver Disease," World Chinese Journal of Digestology 17(12):1212-1217.
Skurk, T. et al. (2004, e-pub. Aug. 28, 2004). "Obesity and Impaired Fibrinolysis: Role of Adipose Production of Plasminogen Activator Inhibitor-1," International Journal of Obesity 28:1357-1364.
Thuy, S. et al. (Dec. 31, 2008). "Nonalcoholic Fatty Liver Disease in Humans is Associated with Increased Plasma Endotoxin and Plasminogen Activator Inhibitor 1 Concentrations and with Fructose Intake," The Journal of Nutrition 138:1452-1455.
Written Opinion for the International Searching Authority, dated Aug. 16, 2017, PCT Application No. PCT/CN2017/089047, 6 pages.
Written Opinion for the International Searching Authority, dated Aug. 25, 2017, PCT Application No. PCT/CN2017/089046, 5 pages.
Written Opinion for the International Searching Authority, dated Sep. 13, 2017, PCT Application No. PCT/CN2017/089052, 5 pages.
Written Opinion for the International Searching Authority, dated Sep. 15, 2017, PCT Application No. PCT/CN2017/089051, 5 pages.
Written Opinion for the International Searching Authority, dated Sep. 20, 2017, PCT Application No. PCT/2017/089048,5 pages.
Written Opinion for the International Searching Authority, dated Sep. 6, 2017, PCT Application No. PCT/CN2017/089049, 4 pages.
Wu, M. et al. (Sep. 23, 2016). "The Research Progress of Relationship Between Lipid Regulation and Diabetic Nephropathy," Medicine and Philosophy 557(9B):66-69. English Abstract.
Zhang, Y. et al. (Apr. 30, 2005). "Fibrinolytic Activity and Type 2 Diabetes Mellitus and Macroangiopathy Thereof," Foreign Medical Sciences 25:42-44. English Abstract.
Jiang, G. et al. (Dec. 31, 1991). "Research Progress of Antithrombotic and Thrombolytic Drugs," Chinese Journal of Biochemical and Pharmaceutics. 1:1-4. English Abstract.
Ma, D. et al. (Aug. 10, 1994). "Molecular Relations Between Thrombosis and Atherosclerosis," Cerebrovascular Diseases Foreign Medical Sciences 2(4):195-197. English Abstract.
Mehta, J. L. et al. (Mar. 1, 1995). "Recombinant Lys-Plasminogen, but Not Glu-Plasminogen, Improves Recombinant Tissue-Type Plasminogen Activator-Induced Coronary Thrombolysis in Dogs," Journal of the American College of Cardiology 25(3):753-760.
Wu, M. et al. (May 15, 2007). "Research of Relationship Between Postprandial Hyperlipidemia, Carotid Atherosclerosis and Fibrinolytic Activity in Patients With Type 2 Diabetes Mellitus," Journal of Shandong University Health Science 45(5):503-506. English Abstract.
Xiao, Q. et al. (Sep. 1997). "Plasminogen Deficiency Accelerates Vessel Wall Disease in Mice Predisposed to Atherosclerosis" Proceedings of the National Academy of Sciences 94:10335-10340.
Yang, S. et al. (Mar. 30, 2002). "Coronary Angiographic Analysis of Coronary Heart Disease Complicated With Type 2 Diabetes," Practical Journal of Medicine & Pharmacy 19(3):164 and 165. English Equivalent Abstract Only.
Ye, P. et al. (Dec. 31, 1998). "The Association of Hypertriglyceridemia with Plasma Haemostatic and Fibrinolytic Activities," Chinese Journal of Arteriosc Lerosis. 6(4):333-335. English Abstract.
Yin, G. et al. (Feb. 28, 2005). "Expression and Purification of the Gene Clone of Human Plasminogen Kringle5 Region," Academic Journal of Shanghai Second Medical University 25(02):151-154. English Abstract.
International Search Report, dated Sep. 14, 2017, PCT Application No. PCT/CN2017/089043, 7 pages.
Written Opinion of the International Searching Authority dated Sep. 14, 2017, PCT Application No. PCT/CN2017/089043, 5 pages.
International Search Report, dated Sep. 8, 2017, PCT Application No. PCT/CN2017/089044, 7 pages.
Written Opinion of the International Searching Authority dated Sep. 8, 2017, PCT Application No. PCT/CN2017/089044, 5 pages.
International Search Report, dated Sep. 8, 2017, PCT Application No. PCT/CN2017/089045, 7 pages.
Written Opinion of the International Searching Authority dated Sep. 8, 2017, PCT Application No. PCT/CN2017/089045, 5 pages.
U.S. Appl. No. 16/469,611, Jinan, L., filed Jun. 13, 2019. (Copy not submitted herewith pursuant to the waiver of 37 C.F.R. § 1.98(a)(2)(iii) issued by the Office on Sep. 21, 2004).

(56) References Cited

OTHER PUBLICATIONS

U.S. Appl. No. 16/469,599, Jinan, L., filed Jun. 13, 2019. (Copy not submitted herewith pursuant to the waiver of 37 C.F.R. § 1.98(a)(2)(iii) issued by the Office on Sep. 21, 2004).
U.S. Appl. No. 16/470,160, Jinan, L., filed Jun. 14, 2019. (Copy not submitted herewith pursuant to the waiver of 37 C.F.R. § 1.98(a)(2)(iii) issued by the Office on Sep. 21, 2004).
U.S. Appl. No. 16/470,173, Jinan, L., filed Jun. 14, 2019. (Copy not submitted herewith pursuant to the waiver of 37 C.F.R. § 1.98(a)(2)(iii) issued by the Office on Sep. 21, 2004).
U.S. Appl. No. 16/470,174, Jinan, L., filed Jun. 14, 2019. (Copy not submitted herewith pursuant to the waiver of 37 C.F.R. § 1.98(a)(2)(iii) issued by the Office on Sep. 21, 2004).
Aisina, R.B. et al. (2014). "Structure and Function of Plasminogen/Plasmin System," Russian Journal of Bioorganic Chemistry 40(6):590-604.
Anderie, K. et al. (1988). "Review of Studies with Plasminogen Concenliates and Proposals for Further Therapeutic Strategies with Plasminogen Concentrates, " Haemostasis 18(Suppl.1):165-175.
Badylak, S.F. (1991). "Enhancement of the Thrombolytic Efficacy of Prourokinase by Lys-Plasminogen in a Dog Model of Artbrial Thrombosis," Thrombosis Research 62:115-126.
Basic Medicine (Dec. 31, 1998). Encyclopedia of Chinese Medicine Shanghai Science and Technology Publishing House. 907:2-3. English Abstract.
Bezerra, J.A. (Dec. 21, 1999). "Plasminogen Deficiency Leads to Impaired Remodeling After a Toxic Injury to the Liver," PNAS 96(26):15143-15148.
Bookstein, J.J. MD et al. (2000). "Plasminogen-Enriched Pulse-Spray Thrombolysis With tPA: Further Developments," Journal of Vascular and Interventional Radiology 11(10):1353-1362.
Butera, D. et al. (Mar. 15, 2015). "NP-000292.1—Plasminogen Isoform 1 Precursor," GenBank 4 pages.
Chang, P.C. et al. (Jan. 1, 2010). "Human Plasminogen Kringle 1-5 Reduces Atherosclerosis and Neointima Formation in Mice by Suppressing the Inflammatory Signaling Pathway," Journal of Thrombosis and Haemostasis 8(1):194-201.
Danese, C. et al. (Nov. 30, 1996). "Lipoproteina(a)e Plasminogeno Nella Malattia Aterosclerotia," Minerva Cardioangiologica 44(11):529-533. Abstract Only.
Das, R. et al. (Mar. 19, 2013). "Macrophage Gene Expression and Foam Cellformation are Regulated by Plasminogen," Circulation 127(11):1209-1218.
Feuerstein, G.Z. et al. (1995). "Cardioprotection and Thrombolysis by Anisliephase in Anesthetized Dogs," Journal of Cardiovascular Pharmacology 25:625-633.
Getz, G.S. et al. (2010). "HDL Apolipoprotein-Related Peptides in the Treatment of Atherosclerosis and Other Inflammatory Disorders," Curr. Pharm. Des. 16(28):3173-3184, 21 pages.
Gong, W. (May 31, 2014). "Clinical Diabetes, Section IV Pathophysiology of Type 2 Diabetes Three Factors, Octet and High Glucose and Lipid Toxicity," ages 6-8. English Abstract.
Hoover-Plow, J. et al. (Dec. 31, 2002). "In Vivo Plasminogen Deficiency Reduces Fat Accumulation," Thromt Haemost. 87:1011-1019.
Huang, C. (Dec. 31, 2003). "Recombinant Tissue Plasminogen Activator Protects Experimental Ischemic Myocardium," Journal of Practical Medicine 19(9):953-954. English Abstract.
Kawao, N. et al. (2010, e-pub. Jan. 10, 2010). "Role of Plasminogen in Macrophage Accumulation During Liver Repair," Thrombosis Research 125:e214-e221.
Kopec, A.K. et al. (Jun. 2016, e-pub. May 4, 2016). "Role of Fibrin(ogen) in Progression of Liver Disease: Guilt by Association?" Semin Thromb Hemost. 42(4):397-407, 18 pages.
Kostka, T. et al. (2009, e-pub. Mar. 28, 2008)."Cardiovascular Disease (CVD) Risk Factors, Physical Activity (PA) and Plasma Plasminogen (Plg) in a Random Sample of Community-Dwelling Elderly," Archives of Gerontology and Geriatrics 48(3):300-305.
Kunadian, V. et al. (Apr. 1, 2012). "Thrombolytic and Myocardial Infarction," Cardiovascular Therapeutics 30(2):e81-e88.
Landskroner, K. et al. (Dec. 31, 2005). "Cross-Species Pharmacologic Evaluation of Plasmin as a Direct-Acting Thrombolytic Agent: Ex Vivo Evaluation for Large Animal Model Development," J Vase Interv Radiol. 16:369-377.
Li, L.-Y. et al. (Mar. 1, 2005). "Angiopoietins and Tie2 in Health and Disease," Pediatric Enoocrinology Reviews 2(3):399-408.
Li, Q. et al. (Feb. 2011). "Research Progress on the Pathogenesis of Diabetic Cardiomyopathy," DC 9(2):291 & 311, 3pgs. English Abstract.
Li, Z. et al. (Apr. 30, 2007). "Research Progress of Liver Trealinent," J. of Liaoning Medical University 28(2):46-48, 4 pages. English Abstract.
Lijnen, H. R. et al. (2007, e-pub. Aug. 23, 2007). "Angiogenesis and Obesity," Cardiovascular Research 78(2):286-293.
Lipek, T. et al. (May 2015). "Obesogenic Environments: Environmental Approaches to Obesity Prevention," J Pediatr Endocrinol Metab. 28(5-6):485-495.
Liu, M.Y. et al. (Oct. 31, 2010). "Plasminogen: Structure, Function and Evolution," Journal of Ocean University of China 40(10):69-74. English Abstract.
LV, W,-S. (Apr. 30, 1990). "The Treatment of Obesity," Guangdong Science and Technology Press, pp. 123-124. English Abstract.
Mayo Clinic (1998). "Heart Failure 1998-2020," 4 pages.
Mitchell, J.W. et al. (Jun. 1, 2006). "Plasminogen Inhibits TNF α-Induced Apoptosis in Monocytes," Blood 107(11):4383-4390.
Morishita, R. et al. (1988). "Novel Therapeutic Atrategy for Atherosclerosis: Ribozyme Oligonucleotides Against Apolipoprotein(a) Selectively Inhibit Apolipoprotein(a) But Not Plasminogen Gene Expression," Circulation 98:1898-1904.
Naito, G. (1986). "The Formulation and Clinical Experience of Plasminogen Activator System," Journal of Japan Society of Blood Transfusion 32(6):590-593. English Abstract.
Nanada, I. (1981). "Effect of Urokinase on Heart and Brain Infarctions Combined With Diabetic Patients," Clinical and Research 58(2):659-665. English Abstract.
Nannan, Z. et al. (Jul. 31, 2014). "Biochemical Testing Technology, Chapter 6 Determination of Glucose in Body Fluid," p. 75. English Abstract.
Neubauer et al. (Apr. 1995). "Accumulation and Cellular Localization of Fibrinogen/Fibrin During Short-Term and Long-Term Rat Liver Injury," Gaslioenterology 108(4):1124-1135.
Okada, K. et al. (Sep. 2008). "Binding of Plasminogen to Hepatocytes Isolated From Injured Mice Liver and Nonparenchymal Cell-Dependent Proliferation of Hepatocytes," Blood Coagulation and Fibrinolysis 19:503-511.
Peng, Y. et al. (Dec. 31, 2005). "Protective Effects of Recombinant Tissue Plasminogen Activator on Acute Myocardial Infarction in Senile Rats," Chinese Journal of Gerontology 25(12):1517-1518. English Abstract.
Pohl, J.F. et al. (Dec. 2001). "Plasminogen Deficiency Leads to Impaired Lobular Reorganization and Matrix Accumulation after Chronic Liver Injury," American Journal of Pathology 159(6):2179-2186.
Schmitz, V. et al. (2007). "Plasminogen Fragment K1-5 Improves Survival in a Murine Hepatocellular Carcinoma Model," Gut 56:271-278.
Schuster, V. et al. (2007). "Plasminogen Deficiency," Journal of Thrombosis and Haemostasis 5:2315-2322.
Science Daily (2008). "How Diabetes Drives Atherosclerosis" 2 pages.
Sha, J. et al. (Mar. 22, 2002). "Plasminogen Reduces Atherosclerosis in Apo(a) Transgenic Mice," Annual Meeting of Professional Research Scientiste on Experimental Biology 16(5):A823.
Shanmukhappa, K. et al. (May 8, 2009). "Plasmin-Mediated Proteolysis is Required for Hepatocyte Growth Factor Activation During Liver Repair," The Journal of Biological Chemistry 284(19):12917-12923.
Shen, Y. et al. (Jun. 14, 2012). "Plasminogen is a Key Proinflammatory Regulator That Accelerates the Healing of Acute and Diabetic Wounds" Thrombosis and Hemostasis, 119(24):5878-5887.
Sima, J. et al. (Apr. 23, 2004, e-pub. Mar. 23, 2004). "The Effect of Angiostatin on Vascular Leakage and VEGF Expression in Rat Retina," FEBS Letters 564(1-2):19-23.

(56) References Cited

OTHER PUBLICATIONS

Sundell, B. et al. (Aug. 5, 1997). "Reduction in Stent and Vascular Graft Thrombosis and Enhancement of Thrombolysis by Recombinant Lys-Plasminogen in Nonhuman Primates," Circulation 96(3):941-948.

Tahara, M. et al. (1999). "Hepatocyte Growth Factor Leads to Recovery From Alcohol-Induced Fatty Liver in Rats," J Clin Invest. 103(3):313-320.

Takamura T. et al., (Mar. 26, 2004). "Genes for Systemic Vascular Complications are Differentially Expressed in the Lives of Type 2 Diabetic Patients," Diabetologia 47:638-647.

Takeshi, A. (1981). "Progress of Thrombolytic Therapy and its Clinical Effect," Blood and Vessel 12(4):493-501. English Abstract.

Tanaka, K. (2000). "PP-1250 Involvement of Tissue Line System in Liver Regenerating: Examination Using Plasminogen Gene Knockout Mice," Journal of Japan Surgical Society 101:520, English Abstract, 3 pages.

Uniprot Protein Database Blast Results, Human Plasminogen Amino Acids 581-808 accessed on Aug. 23, 2020, 5 pages.

Vogten, J.M. et al. (2004, e-pub. Jan. 10, 2004). "Angiostatin Inhibits Experimental Liver Fibrosis in Mice," International Journal of Colorectal Disease 19(4):387-394.

Wang, E. (Sep. 30, 2003). Editor-in-Chief of Pathology, Higher Education Press p. 69. English Abstract.

Wang, G. (Aug. 31, 2007). "Effects of Actilyse on Hemorheology in Rats with Acute Ischemic Myocardial Injure," Chinese Journal of Cardiovascular Rehabilitation Medicine 16(4):369-371, English Abstract.

Wang, L. et al. (Nov. 30, 2004). "Protective Effects of rt-PA on Experimental Myocardial Ischemia in Rats," Journal of Cardiovascular and Pulmonary Diseases 23(4):238-239, English Abstract.

Wang, Z. (Feb. 28, 2007). "Clinical Treatment of Endocrine Diseases and Rational Use of Drug," Scientific and Technological Literature Press pp. 164-176. English Abstract .(Fat Metabolism Disorder).

Xu, B. et al. (Aug. 31, 2014). "Diagnosis and Nursing of Clinical Internal Diseases," Kunming, Yunnan Science and Technology Press, pp. 137-138. English Abstract.

Xu, D. et al. (Feb. 2012). "Therapeutic Effect of Recombinant Tissue Plasminogen Activator on Acute Cerebral Infarction," Prevention and Treatment of Cerebral-Vascular Disease 12(1):37-39. English Abstract.

Xu, L. et al. (Aug. 1, 2012). "Diabetic Angiopathy and Angiogenic Defects," Fibrogenesis & Tissue Repair 5(1):13. 9 pages.

Yang, L. et al. (2004). "Changes of Fbrinolytic Parameters in Coronary Heart Disease," Chinese Journal of Thrombosis and Hemostasis 10(1):8-10. English Abstract.

Yu, D. et al. (Jan. 31, 2009). "Measurements of Plasmin-Alpha2 Antiplasmin Complex in Patients with Liver Cirrohosis and Hepatocarcinoma," Laboratory Medicine and Clinic 6(2):92-93. English Abstract.

Zhang, S.X. et al. (Jan. 4, 2006). "Therapeutic Potential of Angiostatin in Diabetic Nephropathy," J. Am. Soc. Nephrol. 17:475-486, 12 pages.

Zhao, Y. et al. (2009). "The Function of Hemoglutination and Fibrinolysis System Function in Patients With Metabolic Syndrome," Chin. J. Diffic and Compl. Cas. 8(7):1671-6450, 4 pages. English Abstract.

Jia, A. et al. (Oct. 2013). "Evaluation of Fibrinolytic Enzyme in Treatment of Diabetic Cerebral Infarction," Int J Lab Med. 34(19):2614-2616. English Abstract.

Liu, X. (2014). "The Study of Plasmin Combined With Atorvastatin in the Treatment of Cerebral Infarction Patients With Hyperlipidemia," Modern Journal of Integrated Traditional Chinese and Western Medicine 23(31):3490-3491. English Abstract.

Schott, D. et al. (Dec. 3, 1998). "Therapy With a Purified Plasminogen Concentrate in an Infant With Ligneous Conjunctivitisa and Homozygous Plasminogen Deficiency," The New England Jouranal of Medicine 339(23):1679-1685.

Beckman, J.A. et al. (May 15, 2002). "Diabetes and Atherosclerosis: Epidemiology, Pathophysiology, and Management," JAMA 287(19):2570-2581.

BIOSIS (2002). Accession No. 2002-354449, 1 page.

CDC (Oct. 3, 2017). "CDC—Cancers Associated With Overweight and Obesity Make up 40 Percent of Cancers Diagnosed in the United States," Press Release, Retrieved from Internet https://www.cdc.gov/media/releases/2017/p1003-vs-cancer-obesity.html, 3 pages.

* cited by examiner

METHOD FOR PREVENTING AND TREATING FATTY LIVER

CROSS REFERENCE TO RELATED APPLICATIONS

This application is a National Phase application under 35 U.S.C. § 371 of International Application No. PCT/CN2017/089047, filed Jun. 19, 2017, which claims priority to International Application No. PCT/CN2016/110168, filed Dec. 15, 2016, and International Application No. PCT/CN2016/110172, filed Dec. 15, 2016, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000700SEQLIST.TXT, date recorded: Jun. 7, 2019, size: 46 KB).

TECHNICAL FIELD

The present invention relates to a method for preventing and/or treating a fat metabolism disorder and its related conditions, comprising administering an effective amount of plasminogen to a subject susceptible to or suffering from a fat metabolism disorder and its related conditions, to reduce an abnormal fat deposition in a body tissue and an organ, thereby achieving the purpose of preventing and/or treating a fat metabolism disorder and its related conditions and complications.

BACKGROUND ART

The fat metabolism disorder, also known as lipodystrophy, is one of metabolic diseases. It is the abnormality in lipids and lipid metabolites and the amounts thereof in blood and other tissues and organs, caused by primary or acquired factors. Lipid metabolism involves lipids being digested and absorbed in the small intestine, entering the blood circulation via the lymphatic system (via lipoprotein transport), being transformed by the liver, stored in adipose tissues, and being used by tissues when needed. The main function of lipids in the body is to provide energy through oxidation. The adipose tissue is the body's energy store. Fat can also protect the internal organs in cooperation with the skin, bones, and muscles, prevent body temperature loss, and help the absorption of fat-soluble vitamins in food. Phospholipid is an important structural component of all cell membranes. Cholesterol is the precursor of cholic acid and steroid hormones (adrenal cortical hormone and gonadal hormone). Lipid metabolism is regulated by genetics, neurohumor, hormones, enzymes, and tissues and organs such as the liver. When these factors have any abnormalities, it may cause a lipid metabolism disorder and pathophysiological changes of relevant organs, e.g., hyperlipoproteinemia and its resulting clinical syndrome, obesity, fatty liver, etc.

Hyperlipoproteinemia is caused by excessive lipoproteins in blood. Lipids in blood, e.g., triglyceride (TG), free cholesterol (FC), cholesteryl ester (CE) and phospholipid, are rarely soluble in water. Only combined with apolipoproteins (APOs) to form a giant molecule complex (lipoprotein), can these lipids be dissolved, transported and metabolized in blood. Hyperlipemia occurs when blood lipids are above the upper limit in normal people. Hyperlipemia is also called hyperlipoproteinemia since blood lipids are transported in the form of lipoproteins in blood. The general criteria are as follows: fasting blood triglycerides and cholesterol in adults exceed 160 mg/dl and 260 mg/dl, respectively; and cholesterol in children exceeds 160 mg/dl [1].

Hyperlipoproteinemia (hyperlipemia) is one of the important causes of atherosclerotic lesions and is a manifestation of abnormal lipid metabolism in the body. Due to the different types of blood lipids or lipoproteins, the types of blood lipids or lipoproteins of which the contents are beyond the normal range may also be different. Therefore, the World Health Organization (WHO) divides hyperlipoproteinemia into five types: Type I, mainly characterized by an increase in chylomicrons, and opalescent, turbid serum with a high amount of triglycerides (TGs); Type II, which is divided into two subtypes, IIa and IIb, wherein the former is mainly characterized by a significant increase in low-density lipoproteins (LDLs), and the latter is additionally characterized by an increase in very low-density lipoproteins (VLDLs); Type III, characterized by usually turbid serum, an increase in both LDLs and VLDLs, and fusion of the two on the electrophoresis; Type IV, mainly characterized by an increase in VLDLs, and possibly turbid serum; and Type V, characterized by increase in both chylomicrons and VLDLs, and opalescent, turbid serum. Type II and Type IV are the most common [1].

Hyperlipemia can be divided into two categories: primary and secondary, according to the etiology. Primary hyperlipemia is mostly caused by congenital defects (or genetic defects) in lipid and lipoprotein metabolisms and by some environmental factors (comprising diets, nutrition, drugs, etc.) through unknown mechanisms. Secondary hyperlipemia is substantially secondary to certain diseases, such as diabetes mellitus, a liver disease, a kidney disease, a thyroid disease, as well as drinking and obesity. Environmental factors such as diets and lifestyle also contribute to the disease.

Since diabetes mellitus is often associated with a lipid metabolism disorder, diabetes mellitus is also known as "diabetes mellipitus" [2]. The pathogenesis of diabetes mellitus is related to B cell dysfunction and insulin resistance, presenting as chronic hyperglycemia, and a disorder of glucose metabolism is often associated with a disorder of lipid metabolism. The lipid metabolism disorder with diabetes mellitus has become an independent risk factor for a cardiovascular disease, which is substantially manifested by hypertriglyceridemia, a low HDL level, and an increased LDL concentration.

The pathogenesis of the lipid metabolism disorder with diabetes mellitus is still unclear, but numerous evidences show that insulin resistance is the central link of its occurrence. Recent studies have also found that intestinal insulin resistance is also involved. Studies in animal models and populations of diabetes mellitus have shown that abnormalities in the expression of certain genes associated with lipid metabolism further contribute to insulin resistance. The occurrence of atherosclerosis in diabetic patients is related to various factors, but an abnormality in plasma lipid level is the most important factor. Studies have shown that the morbidity and mortality of cardiovascular diseases in diabetic patients are significantly higher than those in non-diabetic patients, and that diabetes mellitus has become an independent risk factor for cardiovascular diseases [3].

In recent years, the relationship between nephropathy and lipid metabolism disorders has attracted more and more attention. A chronic progressive renal injury is often accompanied by abnormal lipid metabolism, and in turn hyperlipemia can promote and aggravate the renal injury, and besides mediating glomerular injury, it also plays a role in a tubulointerstitial injury. Munk first described dyslipidemia in nephrotic syndrome in 1913. Some scholars have reported that hyperlipemia may appear in 70%-10% of patients with nephrotic syndrome. It is mainly manifested by a significant increase in blood total cholesterol (TC) dominated by an increase in low-density lipoprotein cholesterol; and a slight increase in triglyceride (TG), wherein the increase in low-density lipoprotein (LDL) is correlated with urine protein [4]. A patient with chronic renal insufficiency is mainly manifested by moderate triglyceridemia, generally normal plasma total cholesterol level, increased cholesterol in VLDLC and intermediate-density lipoprotein cholesterol (IDLC), decreased high-density lipoprotein cholesterol (HDLC), and increased content of triglyceride in various lipoproteins. The underlying cause is that the uremic environment has adverse effects on the synthesis and catabolism of triglycerides and an inhibitory effect on the reverse transport of cholesterol [5].

With the popularization of kidney transplantation therapy and the wide application of various new immunosuppressive agents (particularly CsA and prednisone), the survival period of patients with chronic renal failure (CRF) has been significantly prolonged, but the incidence of hyperlipemia after kidney transplantation is very high. The main manifestations of hyperlipemia after kidney transplantation are elevated levels of plasma total cholesterol (TC), triglyceride (TG), low-density lipoprotein cholesterol (LDLC), and very low-density lipoprotein cholesterol (VLDLC) [6].

Clinical studies have confirmed that there is a certain correlation between lipid metabolism disorders and diabetic nephropathy. In a diabetic patient with a lipid metabolism disorder, an elevated lipid deposition on a glomerular basement membrane stimulates basement membrane cell proliferation and extracellular matrix formation. As early as in 1936, Kimmelstiel and Wilson found massive lipid depositions in renal arterioles, glomeruli and renal tubules of patients with diabetic nephropathy [7]. Abnormal lipid metabolism leading to glomerular and tubulointerstitial fibrosis is one of the most important causes of progressive renal impairment [8].

Lipid metabolism disorders can also result in occurrence of obesity (obesity syndrome). Obesity is divided into two categories: simple and secondary. Simple obesity refers to obesity without obvious endocrine and metabolic diseases, which can be divided into two types: constitutional obesity and acquired obesity. Constitutional obesity has a family heredity history, patients have been fed with abundant food since childhood, with excess intake, obese since childhood, with hyperplasia and hypertrophy of adipocytes. Acquired obesity is mostly caused by excessive nutrition and/or reduced physical activity, such as caused by the improvement of material conditions of life after middle age, recovery from diseases and full recuperation, and the cessation of physical exercise or physical labor after giving birth; and adipose cells shows hypertrophy change, without hyperplasia, and the therapeutic effect for this type of obesity is better. Secondary obesity is mainly caused by neuroendocrine diseases. Neuroendocrine plays an important role in regulating metabolism: (1) Hypothalamus has the center that regulates appetite; and the sequela of central nervous system inflammation, trauma, tumor and the like can cause hypothalamic dysfunction, making appetite enormous and leading to obesity. (2) Insulin secretion is increased, e.g., hyperinsulinemia is caused by excessive insulin injection in a patient with early non-insulin-dependent diabetes mellitus, and islet B cell tumor secretes excessive insulin, both of which increases fat synthesis, thereby causing obesity. (3) In the case of hypopituitarism, particularly when gonadotrophin and thyrotrophin reduction causes hypogonadism and hypothyroidism, obesity may occur. (4) Multiparas or those orally taking contraceptives for female are predisposed to obesity, suggesting that oestrogen has a role in promoting fat synthesis. (5) Hypercortisolism is often accompanied by centripetal obesity. (6) Hypothyroidism with a low metabolic rate leads to fat accumulation with myxedema. (7) Hypogonadism may also lead to obesity, such as dystrophia adiposogenitalis (also named cerebral adiposity and Frohlich's syndrome, caused by trauma, encephalitis, pituitary tumor, craniopharyngioma and other injuries in the hypothalamus, manifested as centripetal obesity with diabetes insipidus and sexual retardation).

Lipid metabolism disorders often lead to fatty liver. Fatty liver refers to a lesion caused by excessive fat accumulation in liver cells due to various reasons. The liver plays a particularly important role in lipid metabolism, it synthesizes lipoproteins which facilitates lipid transport, and is also a major site for fatty acid oxidation and ketone body formation. The normal content of lipid in liver is not much, about 4%, substantially comprising phospholipid. If the liver cannot transport fat out in time, fat accumulates in the liver cells, thereby forming fatty liver.

Fatty liver can be an independent disease or can be caused by other causes, such as obesity-induced fatty liver, alcoholic fatty liver, rapid weight loss induced fatty liver, malnutrition-induced fatty liver, diabetic fatty liver, drug-induced fatty liver, etc.

Fatty liver may be caused by inhibition of the synthesis of proteins by some drugs or chemical poisons such as tetracycline, adrenocortical hormone, puromycin, cyclohexylamine, emetine, arsenic, lead, silver, and mercury. Hypolipidemic drugs can also result in fatty liver by interfering with lipoprotein metabolism.

One of the hazards of fatty liver is that it promotes the formation of atherosclerosis. One of the causes of atherosclerosis is that a patient with fatty liver is often accompanied by hyperlipemia, and thus blood viscosity is increased, wherein low-density lipoprotein (LDL) can easily penetrate an arterial intima and deposit on a vascular wall due to its extremely small molecular weight, which reduces the arterial elasticity, narrows the vascular diameter, weakens the flexibility, and finally leads to the disturbance of blood circulation. The second hazard of fatty liver is to induce or aggravate hypertension, and coronary heart disease, and easily lead to myocardial infarction and thus sudden death. The third hazard of fatty liver is encephalopathy-liver fatty metamorphosis syndrome (Reye's syndrome). The fourth hazard of fatty liver is to lead to hepatic cirrhosis, liver failure, and liver cancer.

Fatty liver is the product of a lipid metabolism disorder in liver and also the pathogenic factor that aggravates liver injury, which is a development of mutual causation and vicious circle. The lipid droplets in the hepatocytes are increased, resulting in steatosis and enlargement of the hepatocytes, and extrusion of the nuclei away from the center. Fat metabolism mainly takes place in the mitochondria. Fat is transported out of the cell mainly through the smooth endoplasmic reticulum. Fat accumulation in hepatocytes further aggravates the burden of mitochondria and endoplasmic reticulum and reduces their functions, thus affecting the metabolism of other nutrients, hormones and vitamins. Long-term hepatocyte degeneration will lead to regeneration disorder and necrosis of hepatocytes, and thus form liver fibrosis and hepatic cirrhosis. The incidence of hepatocellular carcinoma secondary to hepatic cirrhosis is higher.

The fifth hazard of fatty liver is acute gestational fatty liver with a high mortality. The disease, also known as obstetric acute yellow hepatatrophia, is a rare pregnancy complication with a bad prognosis. The disease occurs mostly in the last three months of pregnancy, and its clinical manifestations are often similar to acute severe liver disease, and comprise acute liver failure, pancreatitis, renal failure, and systemic coagulation abnormality, leading to rapid death. The disease occurs mostly in pregnant women who are pregnant for the first time.

The sixth hazard of fatty liver is to induce or aggravate diabetes mellitus. If the concentration of blood glucose in a patient with obesity-induced fatty liver exceeds the normal level, generally pre-diabetes mellitus is considered true although this situation does not meet the diagnostic criteria of diabetes mellitus. Fatty liver and diabetes mellitus often accompany each other and interact with each other, which brings greater difficulties to clinical treatment.

The studies of the present invention found that plasminogen can prevent and/or reduce an abnormal fat deposition in a body tissue and an organ, for instance, it can prevent and reduce an abnormal lipid deposition in blood, a vascular wall, an internal organ, and a tissue between organs, and improve the function of these tissues and organs, thus providing a new preventive and therapeutic solution for a fat metabolism disorder and its related conditions, as well as the accompanying diseases or complications.

SUMMARY OF THE INVENTION

The present invention relates to the following items:

In one aspect, the present invention relates to: Item 1. A method for preventing and/or treating fatty liver and its related conditions in a subject, comprising administering a prophylactically and/or therapeutically effective amount of plasminogen to the subject, wherein the subject suffers from, is suspected of suffering from fatty liver and its related conditions or has a risk of suffering from fatty liver and its related conditions.

Item 2. The method of item 1, wherein the fatty liver comprises obesity-induced fatty liver, alcohol-induced fatty liver, rapid weight loss induced fatty liver, malnutrition-induced fatty liver, diabetic fatty liver, and drug-induced fatty liver.

In yet another aspect, the present invention relates to: Item 3. A method for preventing and/or treating fatty liver and its related conditions in a subject, comprising administering a prophylactically and/or therapeutically effective amount of plasminogen to the subject, wherein the fatty liver is elicited or accompanied by a disease or condition selected from a group consisting of an endocrine disorder disease, a glucose metabolism disease, a liver disease, a kidney disease, a cardiovascular disease, an intestinal disease, a thyroid disease, a gallbladder or a biliary tract disease, obesity, drinking, and a drug therapy.

Item 4. The method of item 3, wherein the fatty liver is elicited or accompanied by a disease selected from a group consisting of hypertension, diabetes mellitus, chronic hepatitis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and an oestrogen therapy.

In yet another aspect, the present invention relates to: Item 5. A method for preventing and/or treating lipid deposition in liver and its related conditions in a subject, comprising administering a prophylactically and/or therapeutically effective amount of plasminogen to the subject, wherein the subject suffers from, is suspected of suffering from lipid deposition in liver and its related conditions or has a risk of suffering from fatty liver and its related conditions.

Item 6. The method of item 5, wherein the lipid deposition in liver is elicited or accompanied by a disease or condition selected from a group consisting of an endocrine disorder disease, a glucose metabolism disease, a liver disease, a kidney disease, a cardiovascular disease, an intestinal disease, a thyroid disease, a gallbladder or a biliary tract disease, obesity, drinking, and a drug therapy.

Item 7. The method of item 6, wherein the lipid deposition in liver is elicited or accompanied by a disease selected from a group consisting of hypertension, diabetes mellitus, chronic hepatitis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and a drug therapy.

In yet another aspect, the present invention relates to: Item 8. A method for reducing lipid deposition in liver of a subject with atherosclerosis, comprising administering an effective amount of plasminogen to the subject.

In yet another aspect, the present invention relates to: Item 9. A method for reducing lipid deposition in liver of a subject with diabetes mellitus, comprising administering an effective amount of plasminogen to the subject.

In yet another aspect, the present invention relates to: Item 10. A method for reducing lipid deposition in liver of a subject with hyperlipemia, comprising administering an effective amount of plasminogen to the subject.

Item 11. The method of item 10, wherein the hyperlipemia exhibits one or more selected from: elevated serum triglyceride (TG), elevated serum low-density lipoprotein (LDL), and elevated very low-density lipoprotein (VLDL).

Item 12. The method of item 10 or 11, wherein the hyperlipemia comprises hypercholesterolemia, hypertriglyceridemia, combined hyperlipemia, and hypo-high-density lipoproteinemia.

Item 13. The method of any one of items 1 to 12, wherein the plasminogen is administered in combination with one or more other drugs or therapies.

Item 14. The method of item 13, wherein the one or more other drugs comprises a drug for treating diabetes mellitus, a drug for treating atherosclerosis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity.

Item 15. The method of item 14, wherein the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

Item 16. A plasminogen for use in the method of any one of items 1 to 15.

In yet another aspect, the present invention relates to: Item 17. A pharmaceutical composition, comprising a pharmaceutically acceptable carrier and the plasminogen for use in the method of any one of items 1 to 15.

In yet another aspect, the present invention relates to: Item 18. A preventive or therapeutic kit comprising: (i) the plasminogen for use in the method of any one of items 1 to 15, and (ii) a means for delivering the plasminogen to the subject.

Item 19. The kit of item 18, wherein the means is a syringe or a vial.

Item 20. The kit of item 18 or 19, further comprising a label or an instruction for use indicating the administration of the plasminogen to the subject to implement the method of any one of items 1 to 15.

In yet another aspect, the present invention relates to: Item 21. An article of manufacture, comprising:
a container comprising a label; and
(i) the plasminogen for use in the method of any one of items 1 to 15 or a pharmaceutical composition comprising the plasminogen, wherein the label indicates the administration of the plasminogen or the composition to the subject to implement the method of any one of items 1 to 15.

Item 22. The kit of item 20 or the article of manufacture of item 21, further comprising one or more additional means or containers containing other drugs.

Item 23. The kit or the article of manufacture of item 22, wherein the other drugs are selected from one or more of: a drug for treating diabetes mellitus, a drug for treating atherosclerosis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity.

Item 24. The kit or the article of manufacture of item 23, wherein the other drugs are selected from one or more of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

Item 25. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen has at least 75%, 80%, 85%, 90%, 95%, 96%, 97%, 98% or 99% sequence identity with SEQ ID No. 2, 6, 8, 10 or 12, and still has the plasminogen activity.

Item 26. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the plasminogen activity.

Item 27. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is a protein that comprises a plasminogen active fragment and still has the plasminogen activity.

Item 28. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is selected from Glu-plasminogen, Lys-plasminogen, mini-plasminogen, micro-plasminogen, delta-plasminogen or their variants that retain the plasminogen activity.

Item 29. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is a natural or synthetic human plasminogen, or a variant or fragment thereof that still retains the plasminogen activity.

Item 30. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is an ortholog of human plasminogen from a primate or a rodent, or a variant or fragment thereof that still retains the plasminogen activity.

Item 31. The method of any one of items 1 to 15 or the plasminogen of item 16, the pharmaceutical composition of item 17, the kit of any one of items 19 to 20 and 22 to 24 or the article of manufacture of any one of items 21 to 24, wherein the amino acids of the plasminogen are as shown in SEQ ID No. 2, 6, 8, 10 or 12.

Item 32. The method of any one of items 1 to 15 or the plasminogen of item 16, the pharmaceutical composition of item 17, the kit of any one of items 19 to 20 and 22 to 24 or the article of manufacture of any one of items 21 to 24, wherein the plasminogen is a natural human plasminogen.

Item 33. The method of any one of items 1 to 15 or the plasminogen of item 16, the pharmaceutical composition of item 17, the kit of any one of items 19 to 20 and 22 to 24 or the article of manufacture of any one of items 21 to 24, wherein the subject is a human.

Item 34. The method of any one of items 1 to 15 or the plasminogen of item 16, the pharmaceutical composition of item 17, the kit of any one of items 19 to 20 and 22 to 24 or the article of manufacture of any one of items 21 to 24, wherein the subject is lack of or deficient in plasminogen.

Item 35. The method, the plasminogen, the pharmaceutical composition, the kit or the article of manufacture of item 34, wherein the lack or deficiency is congenital, secondary and/or local.

The present invention further relates to the use of plasminogen for implementing the method of any one of items 1 to 15.

The present invention further relates to the use of plasminogen in the preparation of a medicament, a pharmaceutical composition, an article of manufacture, and a kit for the method of any one of items 1 to 15.

The present invention further relates to the prevention and/or treatment of a fat metabolism disorder and its related conditions in a subject.

In one aspect, the present invention relates to a method for preventing and/or treating a fat metabolism disorder and its related conditions in a subject, comprising administering a prophylactically and/or therapeutically effective amount of plasminogen to the subject, wherein the subject is susceptible to a fat metabolism disorder, suffers from a fat metabolism disorder or other diseases accompanied by a fat metabolism disorder. The present invention further relates to the use of plasminogen for preventing and/or treating a fat metabolism disorder and its related conditions in a subject. The present invention further relates to the use of plasminogen in the preparation of a medicament, a pharmaceutical composition, an article of manufacture, and a kit for preventing and/or treating a fat metabolism disorder and its related conditions in a subject. Furthermore, the present invention also relates to a plasminogen for preventing and/or treating a fat metabolism disorder and its related conditions in a subject. The present invention further relates to a medicament, a pharmaceutical composition, an article of manufacture, and a kit comprising plasminogen which are useful for preventing and/or treating a fat metabolism disorder and its related conditions in a subject.

In some embodiments, the fat metabolism disorder is a fat metabolism disorder elicited or accompanied by a disease or condition selected from a group consisting of an endocrine disorder disease, a glucose metabolism disease, a liver disease, a kidney disease, a cardiovascular disease, an intestinal disease, a thyroid disease, a gallbladder or a biliary tract disease, obesity, drinking, and a drug therapy. In some embodiments, the fat metabolism disorder is a fat metabolism disorder elicited or accompanied by a disease selected from a group consisting of hypertension, diabetes mellitus, chronic hepatitis, hepatic cirrhosis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and a drug or hormone therapy. In some embodiments, the fat metabolism disorder is hyperlipemia, hyperlipoproteinemia, fatty liver, atherosclerosis, obesity, and a visceral fat deposition. In still some embodiments, the atherosclerosis comprises aortic atherosclerosis, coronary atherosclerosis, cerebral atherosclerosis, renal atherosclerosis, hepatic atherosclerosis, mesenteric atherosclerosis, and lower limb atherosclerosis.

In yet another aspect, the present invention relates to a method for preventing and/or reducing an abnormal fat deposition in a body tissue and an organ of a subject, comprising administering an effective amount of plasminogen to the subject. The present invention further relates to the use of plasminogen for preventing and/or reducing an abnormal fat deposition in a body tissue and an organ of a subject. The present invention further relates to the use of plasminogen in the preparation of a medicament, a pharmaceutical composition, an article of manufacture, and a kit for preventing and/or reducing an abnormal fat deposition in a body tissue and an organ of a subject. Furthermore, the present invention also relates to a plasminogen for preventing and/or reducing an abnormal fat deposition in a body tissue and an organ of a subject. The present invention further relates to a medicament, a pharmaceutical composition, an article of manufacture, and a kit comprising plasminogen which are useful for preventing and/or reducing an abnormal fat deposition in a body tissue and an organ of a subject.

In yet another aspect, the present invention relates to a method for preventing and/or treating a condition caused by an abnormal fat deposition in a body tissue and an organ of a subject, comprising administering an effective amount of plasminogen to the subject. The present invention further relates to the use of plasminogen for preventing and/or treating a condition caused by an abnormal fat deposition in a body tissue and an organ of a subject. The present invention further relates to the use of plasminogen in the preparation of a medicament, a pharmaceutical composition, an article of manufacture, and a kit for preventing and/or treating a condition caused by an abnormal fat deposition in a body tissue and an organ of a subject. Furthermore, the present invention also relates to a medicament, a pharmaceutical composition, an article of manufacture, and a kit comprising plasminogen which are useful for preventing and/or treating a condition caused by an abnormal fat deposition in a body tissue and an organ of a subject.

In some embodiments, the abnormal fat deposition in a body tissue and an organ refers to an abnormal fat deposition in blood, a subcutaneous tissue, a vascular wall and an internal organ. In some embodiments, the condition resulting from the abnormal fat deposition in a body tissue and an organ comprises obesity, hyperlipemia, hyperlipoproteinemia, fatty liver, atherosclerosis, a lipid-induced cardiac damage, a lipid-induced renal damage, and a lipid-induced islet damage.

In yet another aspect, the present invention relates to a method for preventing and/or treating a condition resulting from a fat metabolism disorder in a subject, comprising administering an effective amount of plasminogen to the subject. The present invention further relates to the use of plasminogen for preventing and/or treating a condition resulting from a fat metabolism disorder in a subject. The present invention further relates to the use of plasminogen in the preparation of a medicament, a pharmaceutical composition, an article of manufacture, and a kit for preventing and/or treating a condition resulting from a fat metabolism disorder in a subject. Furthermore, the present invention also relates to a plasminogen for preventing and/or treating a condition resulting from a fat metabolism disorder in a subject. The present invention further relates to a medicament, a pharmaceutical composition, an article of manufacture, and a kit comprising plasminogen which are useful for preventing and/or treating a condition resulting from a fat metabolism disorder in a subject. In some embodiments, the condition comprises obesity, hyperlipemia, hyperlipoproteinemia, fatty liver, atherosclerosis, a lipid-induced heart tissue injury, and a lipid-induced renal injury.

In yet another aspect, the present invention relates to a method for treating a disease in a subject by reducing an abnormal fat deposition, comprising administering an effective amount of plasminogen to the subject. The present invention further relates to the use of plasminogen for treating a disease in a subject by reducing an abnormal fat deposition. The present invention further relates to the use of plasminogen in the preparation of a medicament, a pharmaceutical composition, an article of manufacture, and a kit for treating a disease in a subject by reducing an abnormal fat deposition. Furthermore, the present invention also relates to a plasminogen for treating a disease in a subject by reducing an abnormal fat deposition. The present invention further relates to a medicament, a pharmaceutical composition, an article of manufacture, and a kit comprising plasminogen which are useful for treating a disease in a subject by reducing an abnormal fat deposition.

In some embodiments, the disease comprises atherosclerosis, coronary heart disease, angina pectoris, myocardial infarction, arrhythmia, fatty liver, hepatic cirrhosis, cerebral ischemia, cerebral infarction, renal insufficiency, nephrotic syndrome, renal insufficiency, and obesity.

In yet another aspect, the present invention relates to a method for preventing and/or treating a lipid-induced injury in a tissue and an organ of a subject, comprising administering an effective amount of plasminogen to the subject. The present invention further relates to the use of plasminogen for preventing and/or treating a lipid-induced injury in a tissue and an organ of a subject. The present invention further relates to the use of plasminogen in the preparation of a medicament, a pharmaceutical composition, an article of manufacture, and a kit for preventing and/or treating a lipid-induced injury in a tissue and an organ of a subject. Furthermore, the present invention also relates to a plasminogen for preventing and/or treating a lipid-induced injury in a tissue and an organ of a subject. The present invention further relates to a medicament, a pharmaceutical composition, an article of manufacture, and a kit comprising plasminogen which are useful for preventing and/or treating a lipid-induced injury in a tissue and an organ of a subject.

In some embodiments, the tissue and the organ comprise an arterial wall, a heart, a liver, a kidney, and a pancreas.

In yet another aspect, the present invention relates to a method for improving hyperlipemia in a subject, comprising administering an effective amount of plasminogen to the subject. The present invention further relates to the use of plasminogen for improving hyperlipemia in a subject. The present invention further relates to the use of plasminogen in the preparation of a medicament, a pharmaceutical composition, an article of manufacture, and a kit for improving hyperlipemia in a subject. Furthermore, the present invention also relates to a plasminogen for improving hyperlipemia in a subject. The present invention further relates to a medicament, a pharmaceutical composition, an article of manufacture, and a kit comprising plasminogen which are useful for improving hyperlipemia in a subject.

In some embodiments, the hyperlipemia is selected from one or more of: hypercholesterolemia, hypertriglyceridemia, combined hyperlipemia, and hypo-high-density lipoproteinemia.

In yet another aspect, the present invention relates to a method for reducing the risk of atherosclerosis in a subject, comprising administering an effective amount of plasminogen to the subject. The present invention further relates to the use of plasminogen for reducing the risk of atherosclerosis in a subject. The present invention further relates to the use of plasminogen in the preparation of a medicament, a pharmaceutical composition, an article of manufacture, and a kit for reducing the risk of atherosclerosis in a subject. Furthermore, the present invention also relates to a plasminogen for reducing the risk of atherosclerosis in a subject. The present invention further relates to a medicament, a pharmaceutical composition, an article of manufacture, and a kit comprising plasminogen which are useful for reducing the risk of atherosclerosis in a subject.

In some embodiments, the subject suffers from hypertension, obesity, diabetes mellitus, chronic hepatitis, hepatic cirrhosis, renal injury, chronic glomerulonephritis, chronic pyelonephritis, nephrotic syndrome, renal insufficiency, kidney transplantation, uremia, hypothyroidism, obstructive cholecystitis, or obstructive cholangitis, or the subject takes a drug or hormone that affects fat metabolism. In some embodiments, the plasminogen reduces the risk of atherosclerosis in a subject in one or more ways selected from: lowering a total cholesterol level, a triglyceride level, and a low-density lipoprotein level in blood, and elevating a high-density lipoprotein level in blood.

In yet another aspect, the present invention relates to a method for treating a disease in a subject by improving hyperlipemia, comprising administering an effective amount of plasminogen to the subject. The present invention further relates to the use of plasminogen for treating a disease by improving hyperlipemia in a subject. The present invention further relates to the use of plasminogen in the preparation of a medicament, a pharmaceutical composition, an article of manufacture, and a kit for treating a disease by improving hyperlipemia in a subject. Furthermore, the present invention also relates to a plasminogen for treating a disease by improving hyperlipemia in a subject. The present invention further relates to a medicament, a pharmaceutical composition, an article of manufacture, and a kit comprising plasminogen which are useful for treating a disease by improving hyperlipemia in a subject.

In some embodiments, the condition comprises diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

In yet another aspect, the present invention relates to a method for preventing and/or treating a hyperlipemia-related condition in a subject, comprising administering an effective amount of plasminogen to the subject. The present invention further relates to the use of plasminogen for preventing and/or treating a hyperlipemia-related condition in a subject. The present invention further relates to the use of plasminogen in the preparation of a medicament, a pharmaceutical composition, an article of manufacture, and a kit for preventing and/or treating a hyperlipemia-related condition in a subject. Furthermore, the present invention also relates to a plasminogen for preventing and/or treating a hyperlipemia-related condition in a subject. The present invention further relates to a medicament, a pharmaceutical composition, an article of manufacture, and a kit comprising plasminogen which are useful for preventing and/or treating a hyperlipemia-related condition in a subject. In some embodiments, the condition comprises diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

In any of the above-mentioned embodiments of the present invention, the plasminogen is administered in combination with one or more other drugs or therapies. In some embodiments, the one or more other drugs comprises a drug for treating hypertension, a drug for treating diabetes mellitus, a drug for treating atherosclerosis, a drug for treating chronic glomerulonephritis, a drug for treating chronic pyelonephritis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity. In some embodiments, the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine. In some further embodiments, the drugs comprise hypolipidemic drugs: statins; fibrates; niacin; cholestyramine; clofibrate; unsaturated fatty acids such as Yishouning, Xuezhiping, and Xinmaile; and alginic sodium diester; anti-platelet drugs: aspirin; dipyridamole; clopidogrel; and cilostazol; vasodilators: hydralazine; nitroglycerin, and isosorbide dinitrate; sodium nitroprusside; α1-receptor blockers such as prazosin; α-receptor blockers such as phentolamine; β2-receptor stimulants such as salbutamol; captopril, enalapril; nifedipine, diltiazem; and salbutamol, loniten, prostaglandin, and atrial natriuretic peptide; thrombolytic drugs: urokinase, and streptokinase; tissue-type plasminogen activators; single chain urokinase-type plasminogen activators; and a TNK tissue-type plasminogen activator; and anticoagulant drugs: heparin; enoxaparin; nadroparin; and bivalirudin.

In any of the above-mentioned embodiments of the present invention, the plasminogen may have at least 75%, 80%, 85%, 90%, 95%, 96%, 97%, 98% or 99% sequence identity with SEQ ID No. 2, 6, 8, 10 or 12, and still have the activity of plasminogen. In some embodiments, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the activity of plasminogen.

In some embodiments, the plasminogen is a protein that comprises a plasminogen active fragment and still has the activity of plasminogen. In some embodiments, the plasminogen is selected from Glu-plasminogen, Lys-plasminogen, mini-plasminogen, micro-plasminogen, delta-plasminogen or their variants that retain the plasminogen activity. In some embodiments, the plasminogen is a natural or synthetic human plasminogen, or a variant or fragment thereof that still retains the plasminogen activity. In some embodiments, the plasminogen is an ortholog of human plasminogen from a primate or a rodent, or a variant or fragment thereof that still retains the plasminogen activity. In some embodiments, the amino acids of the plasminogen are as shown in SEQ ID No. 2, 6, 8, 10 or 12. In some embodiments, the plasminogen is a natural human plasminogen.

In some embodiments, the subject is a human. In some embodiments, the subject is lack of or deficient in plasminogen. In some embodiments, the lack or deficiency is congenital, secondary and/or local.

In some embodiments, the pharmaceutical composition comprises a pharmaceutically acceptable carrier and the plasminogen for use in the above-mentioned method. In some embodiments, the kit may be a preventive or therapeutic kit comprising: (i) the plasminogen for use in the above-mentioned method, and (ii) a means for delivering the plasminogen to the subject. In some embodiments, the means is a syringe or a vial. In some embodiments, the kit further comprises a label or an instruction for use indicating the administration of the plasminogen to the subject to implement any one of the above-mentioned methods.

In some embodiments, the article of manufacture comprising: a container comprising a label; and (i) the plasminogen for use in the above-mentioned methods or a pharmaceutical composition comprising the plasminogen, wherein the label indicates the administration of the plasminogen or the composition to the subject to implement any one of the above-mentioned methods.

In some embodiments, the kit or the article of manufacture further comprises one or more additional means or containers containing other drugs. In some embodiments, the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

In some embodiments of the above-mentioned method, the plasminogen is administered by systemic or topical route, preferably by the following routes: intravenous, intramuscular, and subcutaneous administration of plasminogen for treatment. In some embodiments of the above-mentioned method, the plasminogen is administered in combination with a suitable polypeptide carrier or stabilizer. In some embodiments of the above-mentioned method, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily.

The present invention explicitly encompasses all the combinations of technical features belonging to the embodiments of the present invention, and these combined technical solutions have been explicitly disclosed in the present application, as if the above-mentioned technical solutions were individually and explicitly disclosed. In addition, the present invention also explicitly encompasses all the combinations between various embodiments and elements thereof, and the combined technical solutions are explicitly disclosed herein.

Definition

The "fat metabolism disorder" of the present invention, also known as "abnormal fat metabolism" and "lipodystrophy", is the generic term for the clinical or pathological manifestations caused by the abnormality, disorder or dysfunction of fat metabolism. "Fat metabolism disorder", "abnormal fat metabolism", and "lipodystrophy" are used interchangeably herein. "Fat metabolism", "lipid metabolism", and "metabolism of lipids" are used interchangeably in the present invention.

"A fat metabolism disorder-related condition" is the generic term for the conditions related to fat metabolism disorder. The expression "related" may be etiology-, pathogenesis-, pathogenic manifestation-, clinical symptom- and/or therapeutic principle-related.

"Blood lipid" is the generic term for triglycerides, cholesterol and phospholipids. Lipoprotein is a globular macromolecular complex composed of apolipoproteins and blood lipids. Since lipoprotein is composed of different components, cholesterol and triglycerides, at different densities, it is divided into 5 categories: chylomicron (CM), very low-density lipoprotein (VLDL), intermediate density lipoprotein (IDL), low-density lipoprotein (LDL), and high-density lipoprotein (HDL). According to the blood lipid risk level, the most common clinical types of dyslipoproteinemia are: hypercholesterolemia, hypertriglyceridemia, combined hyperlipemia, and hypo-high-density lipoproteinemia. Secondary dyslipidemia is commonly found in diabetes mellitus, hypothyroidism, nephrotic syndrome, kidney transplantation, a severe liver disease, an obstructive biliary tract disease, obesity, drinking, and drug therapy such as oestrogen therapy, etc. Primary dyslipidemia can be considered if secondary dyslipidemia can be ruled out.

"Hyperlipemia" refers to a pathological condition in which blood lipid components such as cholesterol, triglycerides, phospholipids and non-lipidated fatty acids are elevated in plasma.

"A hyperlipemia-related condition" refers to a condition of which etiology, pathogenesis, pathogenic manifestations, clinical symptoms and/or therapeutic principle are related to hyperlipemia. Preferably, the condition includes but is not limited to diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

Abnormalities of one or several lipids in plasma due to abnormal fat metabolism or turnover are referred to as "hyperlipemia", "hyperlipidemia" or "dyslipidemia".

Lipids are insoluble or slightly soluble in water, and must bind to proteins to form lipoproteins to function in the blood circulation. Therefore, hyperlipemia is often a reflection of "hyperlipoproteinemia".

The "hyperlipemia-related condition" of the present invention is also known as "hyperlipidemia-related condition" and "hyperlipoproteinemia-related condition".

"Fatty liver" refers to a lesion of excessive accumulation of fat in hepatocytes due to various causes. It can be an independent disease or can be caused by other causes, such as obesity-induced fatty liver, alcohol-induced fatty liver, rapid weight loss induced fatty liver, malnutrition-induced fatty liver, diabetic fatty liver, drug-induced fatty liver, etc.

In the case of fatty liver, the lipid droplets in the hepatocytes are increased, resulting in steatosis and enlargement of the hepatocytes, and extrusion of the nuclei away from the center. Fat metabolism mainly takes place in the mitochondria. Fat is transported out of the cell mainly through the smooth endoplasmic reticulum. Fat accumulation in hepatocytes further aggravates the burden of mitochondria and endoplasmic reticulum and reduces their functions, thus affecting the metabolism of other nutrients, hormones and vitamins. Long-term hepatocyte degeneration will lead to regeneration disorder and necrosis of hepatocytes, and thus form liver fibrosis and hepatic cirrhosis.

"Atherosclerosis" is a chronic, progressive arterial disease in which the fat deposited in the arteries partially or completely blocks blood flow. Atherosclerosis occurs when the otherwise smooth and solid arterial intima becomes roughened and thickened and is blocked by fat, fibrin, calcium, and cellular debris. Atherosclerosis is a progressive process. When the concentration of lipids in the blood is greatly increased, fatty streaks form along the arterial wall. These streaks can lead to deposits of fat and cholesterol, which attach to the otherwise smooth arterial intima and thus form nodules. Underneath these nodules, fibrotic scar tissue develops, leading to calcium deposition. The calcium deposits gradually develop into a chalky hard film (referred to as atherosclerotic plaque) that cannot be removed. This permanent film inside the artery would block the normal expansion and contraction of the artery, which slows the blood flow velocity within the artery, making the blood easy to form clots that block or stop blood flowing through the artery.

The exact cause of atherosclerosis has not been determined. However, important pathogenic factors have been identified as hyperlipemia, hypertension, a history of smoking, a family history of atherosclerosis (suffering from the disease before the age of 60) or diabetes mellitus. Hyperlipemia can promote the formation of fatty streaks. Hypertension exerts a constant force on the arteries, accelerating the process of arterial occlusion and arteriosclerosis; therefore, it can increase the prevalence of atherosclerosis. Smoking can cause arterial contractions and restrict blood flow, thus setting the stage for arterial occlusion. Diabetes mellitus can also contribute to the development of atherosclerosis, especially in very small arteries.

In the case of atherosclerosis alone, people do not feel any symptoms. The disease is only discovered when an artery connected to a vital organ in the body is blocked. Symptoms are more pronounced when arteries in the organ are blocked. For instance, people may feel angina pectoris if the cardiac feeding artery is partially blocked; however, if it is completely blocked, it may lead to a heart disease (the death of heart tissue fed by the blocked artery). If atherosclerosis affects the cerebral arteries, people may experience dizziness, blurred vision, syncope, and even a stroke (the death of brain tissue fed by the blocked arteries, resulting in a nerve damage, such as paralysis of a limb controlled by dead brain tissue). Occlusion of arteries to the kidneys may also lead to renal failure. Occlusion of blood vessels to the eyes may lead to blindness. Occlusion of arteries in the extremities may lead to lesions in each limb.

Atherosclerosis is the main cause of coronary heart disease, cerebral infarction, and peripheral vascular disease. Lipid metabolism disorder is the pathological basis of atherosclerosis, wherein the lesion of affected artery begins from intima, where accumulation of lipids and compound carbohydrates, hemorrhage and thrombosis first appear generally, followed by hyperplasia of fibrous tissue and calcinosis, with gradual metamorphosis and calcification of the arterial medial layer, leading to thickening and hardening of the arterial wall, and stenosis of vascular lumen. The lesion generally involves the large and medium muscular arteries. Once the lesion has developed enough to block the arterial lumen, the tissues or organs supplied by the artery will become ischemic or necrotic.

Atherosclerosis is a systemic disease, and the occurrence of an atherosclerotic lesion in the blood vessels of an organ means that blood vessels elsewhere may already have had the same lesion; similarly, a vascular event in an organ means an increased risk of vascular event elsewhere.

DETAILED DESCRIPTION OF EMBODIMENTS

Plasmin is a key component of the plasminogen activation system (PA system). It is a broad-spectrum protease that can hydrolyze several components of the extracellular matrix (ECM), including fibrin, gelatin, fibronectin, laminin, and proteoglycan [9]. In addition, plasmin can activate some pro-matrix metalloproteinases (pro-MMPs) to form active matrix metalloproteinases (MMPs). Therefore, plasmin is considered to be an important upstream regulator of extracellular proteolysis [10,11]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. The activity of PAs is simultaneously inhibited by the plasminogen activator inhibitor-1 (PAI-1) of uPA and tPA and regulated by the plasminogen activator inhibitor-2 (PAI-2) that primarily inhibits uPA. There are uPA-specific cell surface receptors (uPARs) that have direct hydrolytic activity on certain cell surfaces [12,13].

Plasminogen is a single-stranded glycoprotein composed of 791 amino acids and has a molecular weight of about 92 kDa[14,15]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids [16,17]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease [18]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered plasminogen is a 38 kDa fragment, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis [19]. Plasmin also has substrate specificity for several components of ECM, including laminin, fibronectin, proteoglycan and gelatin, indicating that plasmin also plays an important role in ECM remodeling[15,20,21]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis [22]. In addition, plasmin has the ability to activate certain potential forms of growth factors [23-25]. In vitro, plasmin can also hydrolyze components of the complement system and release chemotactic complement fragments.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No. 4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No. 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain [26,27]. The amino acid sequence (SEQ ID No. 8) of δ-plasminogen has been reported in the literature [27], and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid) [28]; the amino acid sequence is as shown in SEQ ID No. 10; and the cDNA sequence encoding this amino acid sequence is as shown in SEQ ID No. 9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid) [29], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "plasminogen" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No.14, or an amino acid sequence having an amino acid sequence identity of at least 80%, 90%, 95%, 96%, 97%, 98% or 99% with SEQ ID No.14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction X/Y×100 wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the anti-Tau antibody of the present invention (e.g., a polynucleotide encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEENTM, PLURONICSTM or polyethylene glycol (PEG). Preferred lyophilized anti-VEGF antibody formulations are described in WO 97/04801, which is incorporated herein by reference.

The formulations of the invention may also comprise one or more active compounds required for the particular condition to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and γ ethyl-L-glutamic acid (Sidman et al. Biopolymers 22:547(1983)), non-degradable ethylene-vinyl acetate (Langer et al. supra), or degradable lactic acid-glycolic acid copolymers such as Lupron DepotTM (injectable microspheres composed of lactic acid-glycolic acid copolymer and leuprolide acetate), and poly D-(–)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulthydryl residues, lyophilizing from acidic solutions, controlling moisture content, using appropriate additives, and developing specific polymer matrix compositions.

Administration and Dosage

The pharmaceutical composition of the present invention is administered in different ways, for example by intravenous, intraperitoneal, subcutaneous, intracranial, intrathecal, intraarterial (e.g., via carotid), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

Articles of Manufacture or Kits

One embodiment of the present invention relates to an article of manufacture or a kit comprising plasminogen of the present invention or plasmin useful in the treatment of angiocardiopathy and its related conditions caused by diabetes mellitus. The article preferably includes a container, label or package insert. Suitable containers include bottles, vials, syringes and the like. The container can be made of various materials, such as glass or plastic. The container contains a composition that is effective to treat the disease or condition of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the angiocardiopathy and its related conditions caused by diabetes mellitus according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to direct a user of the composition to administer to a patient the plasminogen composition and other drugs for treating an accompanying disease.

EXAMPLES

Example 1 Plasminogen Ameliorates Lipid Deposition in Liver of Diabetic Mice

Ten 24- to 25-week-old male db/db mice were randomly divided into two groups, five in the control group administered with vehicle PBS and five in the group administered with plasminogen, respectively. The mice were weighed and grouped on the day when the experiment began, i.e. day 0. Plasminogen or PBS was administered from day 1. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein, both lasting for 35 consecutive days. The mice were sacrificed on Day 36. The liver tissues were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s followed by nuclear staining with hematoxylin for 30 s, and sealing with glycerine and gelatin. The sections were observed under an optical microscope at 200×.

Figure 1:
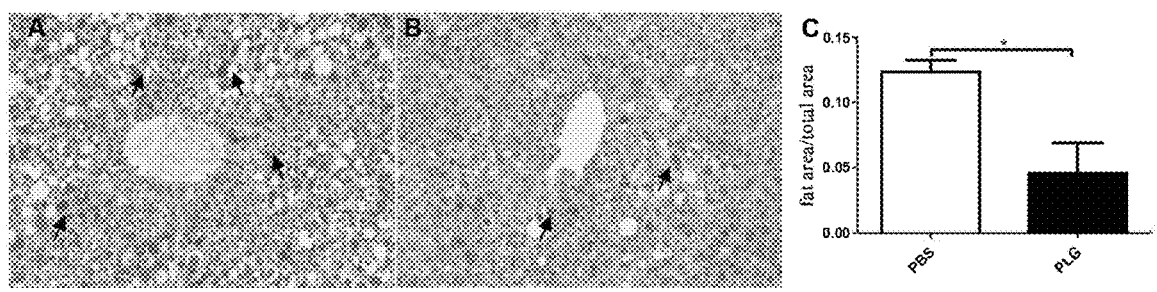
FIG. 1 shows an image of oil red O staining of liver after administration of plasminogen to 24- to 25-week diabetic mice for 35 days. The results showed that the lipid deposition area in liver of mice in the group administered with plasminogen was significantly less than that in the control group administered with vehicle PBS, and the statistical difference was significant (* indicates P<0.05). It indicates that plasminogen can reduce fat deposition in liver of diabetic mice.

The staining results showed that the lipid deposition area in liver of mice in the group administered with plasminogen (FIG. 1B) was significantly lower than that in the control group administered with vehicle PBS (FIG. 1A), and the statistical difference was significant (P=0.02) (FIG. 1C). It indicates that plasminogen can reduce fat deposition in liver of diabetic mice.

Example 2 Plasminogen Ameliorates Lipid Deposition in Liver of ApoE Atherosclerosis Mice Thirteen 6-week-old male ApoE mice were fed with a high-fat and high-cholesterol diet (Nantong TROPHIC, TP2031) for 16 weeks to induce the atherosclerosis model [30,31]. The model mice continued to be fed with a high-fat and high-cholesterol diet. 50 μL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. The mice were sacrificed on Day 31. The liver tissues were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 200×.

Figure 2:
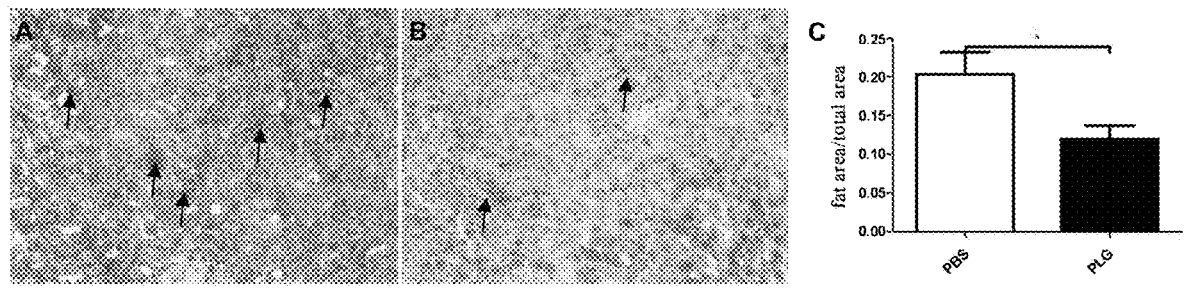
FIG. 2 shows a representative image of oil red O staining of liver after administration of plasminogen to ApoE atherosclerosis model mice for 30 days. A represents the control group administered with vehicle PBS, B represents the group administered with plasminogen, and C represents the quantitative analysis results. The results showed that the fat deposition in liver of mice in the group administered with plasminogen was remarkably lower than that in the control group administered with vehicle PBS, and the quantitative analysis showed significant statistical difference (* indicates P<0.05). It indicates that plasminogen can reduce fat deposition in liver of atherosclerosis model mice.

The staining results showed that the fat deposition in liver of mice in the group administered with plasminogen (FIG. 2B) was remarkably lower than that in the control group administered with vehicle PBS (FIG. 2A), and the quantitative analysis showed significant statistical difference (P=0.02) (FIG. 2C). It indicates that plasminogen can reduce fat deposition in liver of atherosclerosis model mice.

Example 3 Plasminogen Reduces the Fat Deposition in Liver of 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The livers were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 200×.

Figure 3:
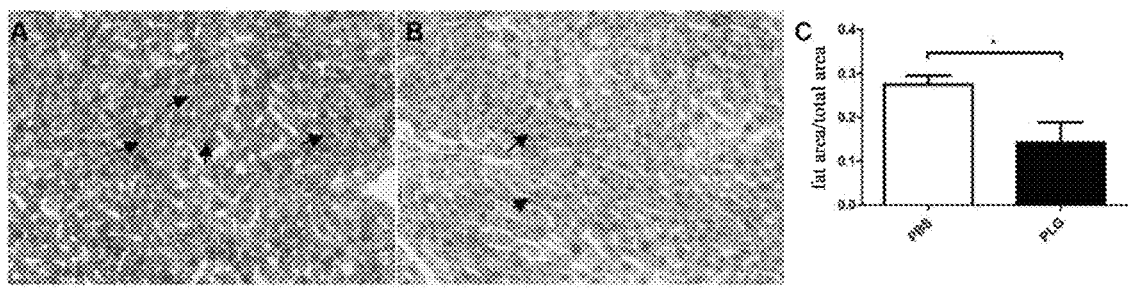
FIG. 3 shows observed results of oil red O staining of liver after administration of plasminogen to 16-week hyperlipemia model mice for 30 days. A represents the control group administered with vehicle PBS, B represents the group administered with plasminogen, and C represents the quantitative analysis results. The results showed that the fat deposition in liver of mice in the group administered with plasminogen was remarkably lower than that in the control group administered with vehicle PBS, and the quantitative analysis showed significant statistical difference (* indicates P<0.05). It indicates that plasminogen can ameliorate fat deposition in liver of hyperlipemia model mice.

Oil red O staining can show lipid deposition and reflect the extent of lipid deposition [34]. The results showed that the fat deposition in liver of mice in the group administered with plasminogen (FIG. 3B) was remarkably lower than that in the control group administered with vehicle PBS (FIG. 3A), and the quantitative analysis showed significant statistical difference (FIG. 1C). It indicates that plasminogen can reduce fat deposition in liver of hyperlipemia model mice.

Figure 4:
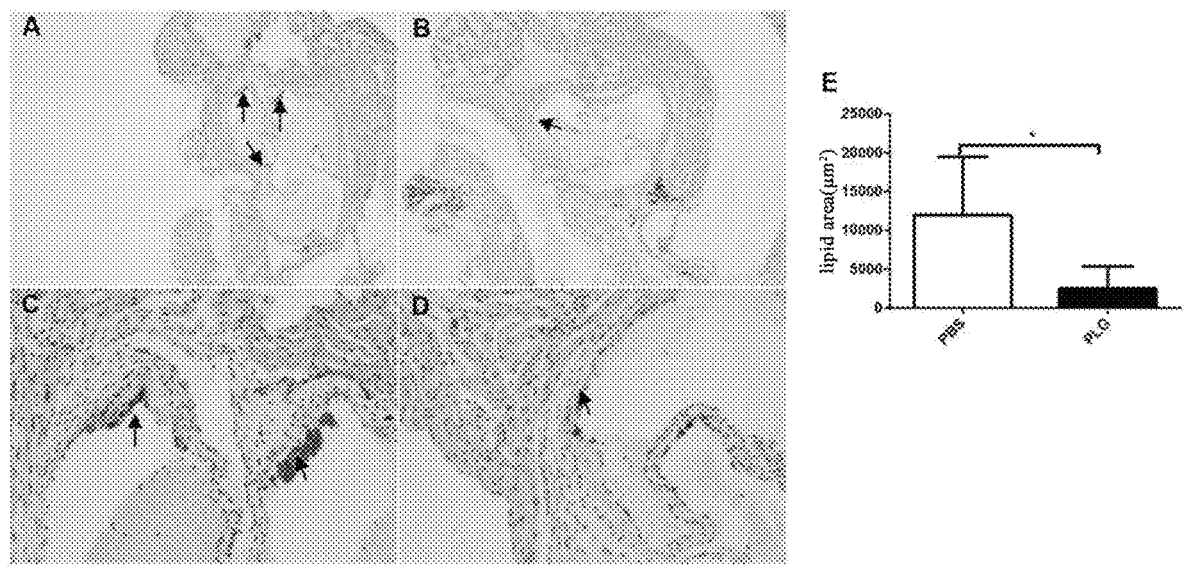
FIG. 4 shows observed results of oil red O staining of aortic sinus after administration of plasminogen to 16-week hyperlipemia model mice for 30 days. A and C represent the control group administered with vehicle PBS, B and D represent the group administered with plasminogen, and E represents the quantitative analysis results. The results showed that the fat deposition in aortic sinus of mice in the group administered with plasminogen was remarkably lower than that in the control group administered with vehicle PBS, and the statistical difference was significant (* indicates P<0.05). It indicates that plasminogen can ameliorate fat deposition in aortic sinus of hyperlipemia model mice.

Example 4 Plasminogen Reduces Lipid Deposition in Aortic Sinus of 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours, then sedimented in 15% and 30% sucrose at 4° C. overnight, respectively, and embedded in OCT. The frozen sections of aortic sinus were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 40×(FIGS. 4A and 4B) and 200×(FIGS. 4C and 4D).

The results showed that the fat deposition in aortic sinus of mice in the group administered with plasminogen (FIGS. 4B and 4D) was remarkably lower than that in the control group administered with vehicle PBS (FIGS. 4A and 4C), and the statistical difference was significant (FIG. 2E). It indicates that plasminogen can reduce lipid deposition in aortic sinus of hyperlipemia model mice.

Figure 5:
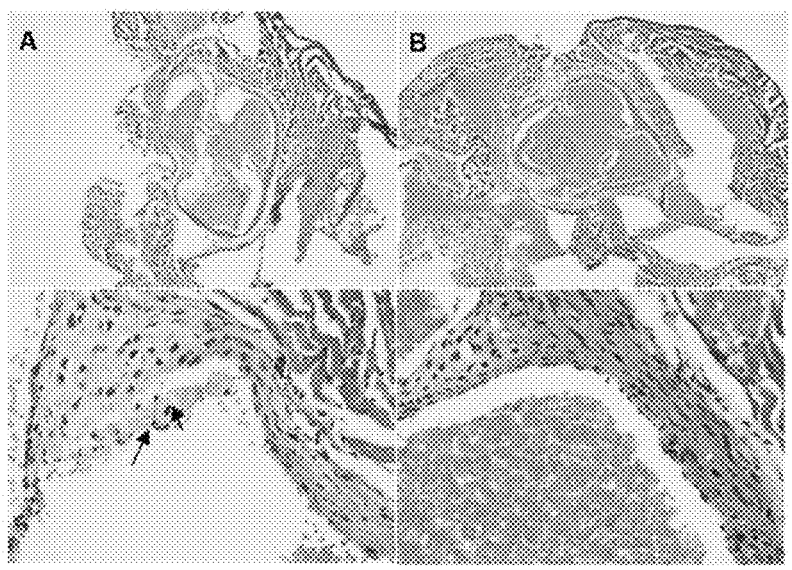
FIG. 5 shows a representative image of HE staining of aortic sinus after administration of plasminogen to 16-week hyperlipemia model mice for 30 days. A and C refer to the control group administered with vehicle PBS, and B and D refer to the group administered with plasminogen. The results showed that the foam cell deposition (indicated by arrow) and the plaque deposition on the aortic wall in the control group administered with vehicle PBS were severe; while in the group administered with plasminogen, only a mild foam cell deposition was observed on the aortic wall, no obvious atherosclerotic plaque deposition was observed under the intima, and the aortic injury in the group administered with plasminogen was relatively minor. It indicates that plasminogen can ameliorate the injury caused by lipid deposition on the inner wall of aortic sinus of hyperlipemia model mice.

Example 5 Plasminogen Improves Aortic Sinus Injury in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The fixed tissue samples were paraffin-embedded after dehydration with alcohol gradient and permeabilization with xylene. The aortic sinus tissue sections were 3 μm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 40×(FIGS. 5A and B) and 200×(FIGS. 5C and D).

The results showed that the foam cell deposition (indicated by arrow) and the plaque deposition on the inner wall of aortic sinus in the control group administered with vehicle PBS (FIGS. 3A and C) were severe; while in the group administered with plasminogen (FIGS. 3B and D), only a mild foam cell deposition was observed on the inner wall of aortic sinus, no obvious atherosclerotic plaque deposition was observed under the intima, and the injury to the inner wall of aortic sinus in the group administered with plasminogen was relatively minor. It indicates that plasminogen can ameliorate the damage to the inner wall of arterial sinus of hyperlipemia model mice.

Example 6 Plasminogen Reduces Expression of Cardiac Fibrin in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 30 minutes, and after the time was up, the goat serum liquid was discarded, and the tissues were circled with a PAP pen. The sections were incubated with 3% hydrogen peroxide for 15 minutes and washed with water twice for 5 minutes each time. The sections were incubated with rabbit anti-mouse fibrin antibody (Abcam) overnight at 4° C. and washed with 0.01M PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Fibrinogen is the precursor of fibrin, and in the presence of tissue injury, as a stress response to the body's injury, fibrinogen is hydrolyzed into fibrin and deposited at the injury site [35,36]. Therefore, the local fibrin level at the injury site can be used as a sign of the degree of injury.

Figure 6:
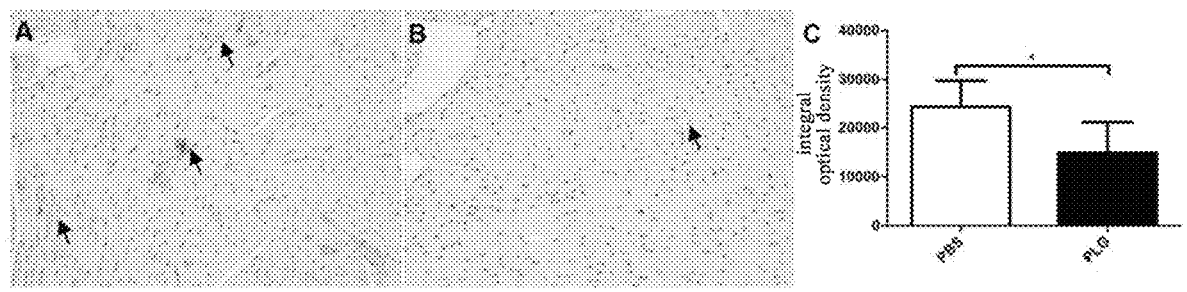
FIG. 6 shows an image of immunohistochemical staining of cardiac fibrin after administration of plasminogen to 16-week hyperlipemia model mice for 30 days. A represents the control group administered with vehicle PBS, B represents the group administered with plasminogen, and C represents the quantitative analysis results. The results showed that the positive expression of cardiac fibrin in mice in the group administered with plasminogen was remarkably lower than that in the control group administered with vehicle PBS, and the statistical difference was significant (* indicates P<0.05). It indicates that plasminogen can reduce the cardiac injury caused by hyperlipemia.

The immunohistochemical staining results showed that the positive expression of cardiac fibrin in mice in the group administered with plasminogen (FIG. 6B) was remarkably less than that in the control group administered with vehicle PBS (FIG. 6A), and the statistical difference was significant (FIG. 6C), indicating that plasminogen can reduce a myocardial injury caused by hyperlipemia.

Example 7 Plasminogen Protects 16-Week Hyperlipemia Model Mice from Myocardial Injury Effectively Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The thickness of the tissue sections was 3 µm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 30 minutes, and after the time was up, the goat serum liquid was discarded, and the tissues were circled with a PAP pen. The sections were incubated with 3% hydrogen peroxide for 15 minutes and washed with water twice for 5 minutes each time. The sections were incubated with goat anti-mouse IgM (HRP) antibody (Abcam) for 1 hour at room temperature and washed with PBS twice for 5 minutes each time. The sections were developed with a DAB kit (Vector laboratories, Inc., USA). After washed with water three times, the sections were subjected to nuclear staining with hematoxylin for 30 seconds and flushing with running water for 5 minutes. After dehydration with alcohol gradient, permeabilization with xylenehe, and sealing with a neutral gum, the sections were observed under an optical microscope at 200×.

IgM antibodies play an important role during the clearance of apoptotic and necrotic cells, and the local level of IgM antibodies in damaged tissues and organs is positively correlated with the degree of injury [37,38]. Therefore, detection of local level of IgM antibodies in tissues and organs can reflect the extent of injury of the tissues and organs.

Figure 7:
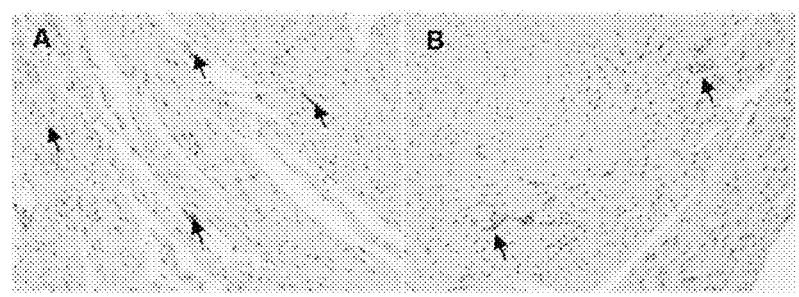
FIG. 7 shows a representative image of IgM immunostaining of heart after administration of plasminogen to 16-week hyperlipemia model mice for 30 days. A represents the control group administered with vehicle PBS, and B represents the group administered with plasminogen. The results showed that the positive expression of IgM in the heart of mice in the group administered with plasminogen was remarkably less than that in the control group administered with vehicle PBS, indicating that plasminogen can alleviate the cardiac injury caused by hyperlipemia.

The immunostaining results showed that the positive expression of IgM in the heart of mice in the group administered with plasminogen (FIG. 7B) was remarkably less than that in the control group administered with vehicle PBS (FIG. 7A), indicating that plasminogen can reduce the cardiac injury in hyperlipemia model animals.

Example 8 Plasminogen Alleviates Cardiac Fibrosis in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The tissue sections was 3 µm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Sirius red staining allows for long-lasting staining of collagen. As a special staining method for pathological sections, Sirius red staining can show the collagen tissue specifically.

Figure 8:
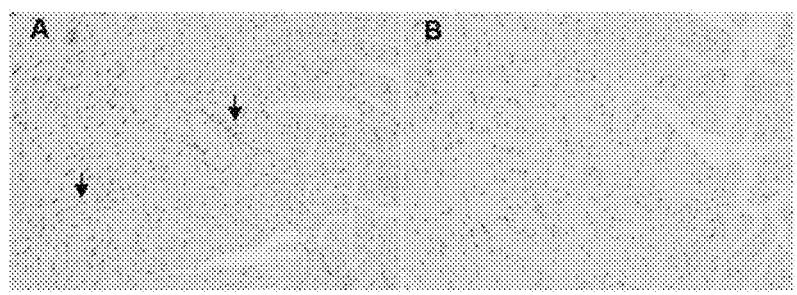
FIG. 8 shows a representative image of Sirius red staining of heart after administration of plasminogen to 16-week hyperlipemia model mice for 30 days. A represents the control group administered with vehicle PBS, and B represents the group administered with plasminogen. The results showed that the collagen deposition in the group administered with plasminogen was remarkably less than that in the control group administered with vehicle PBS, indicating that plasminogen can alleviate the cardiac fibrosis in hyperlipemia model mice.

The staining results showed that the deposition of collagen in the group administered with plasminogen (FIG. 8B) was remarkably less than that in the control group administered with vehicle PBS (FIG. 8A), indicating that plasminogen can reduce the deposition of collagen in the heart tissues of hyperlipemia model mice and alleviate myocardial fibrosis.

Example 9 Plasminogen Repairs Myocardial Injury in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. After administration on Day 30, the mice began to fast for 16 hours, and on Day 31, the blood was collected from removed eyeballs, and centrifuged to obtain a supernatant, which was detected for the concentration of troponin in serum using cardiac troponin (Cardiac troponin I, CTNI) detection kit (Nanjing Jiancheng).

Cardiac troponin I is an important marker of myocardial injury, and its serum concentration can reflect the extent of myocardial injury [39].

Figure 9:
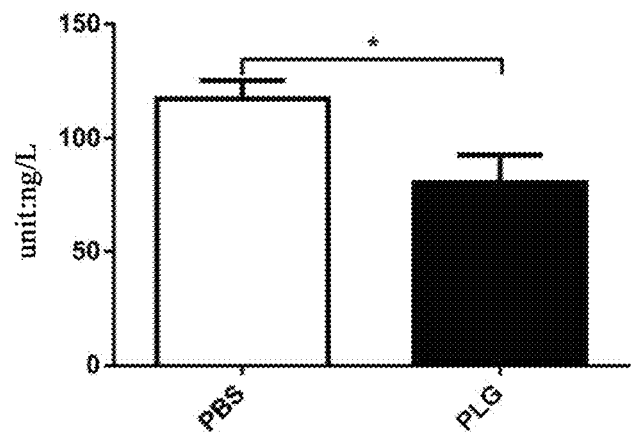
FIG. 9 shows detection results of serum troponin after administration of plasminogen to 16-week hyperlipemia model mice for 30 days. The results showed that the concentration of cardiac troponin in serum in the control group administered with vehicle PBS was remarkably higher than that in the group administered with plasminogen, and the statistical difference was significant (* indicates P<0.05). It indicates that plasminogen can significantly repair the damage to hyperlipidemic heart.

The detection results showed that the concentration of cardiac troponin in serum in the control group administered with vehicle PBS was remarkably higher than that in the group administered with plasminogen, and the statistical difference was significant (FIG. 9). It indicates that plasminogen can significantly ameliorate the cardiac injury in hyperlipemia model mice.

Example 10 Plasminogen Increases the Concentration of Serum High-Density Lipoprotein Cholesterol in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with a 3% cholesterol high-fat diet. 50 μL of blood was taken from each mouse three days before administration, and the total cholesterol was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 20 days. On Day 10 and Day 20, the mice fasted for 16 hours, and on Day 11 and Day 21, 50 μL of blood was collected from orbital venous plexus, and centrifuged to obtain a supernatant, which was used in detecting the serum high-density lipoprotein cholesterol (HDL-C). The content of high-density lipoprotein cholesterol herein was detected by the method as described in a detection kit (Nanjing Jiancheng Bioengineering Institute, Cat #A112-1).

High-density lipoprotein is an anti-atherosclerosis plasma lipoprotein, a protective factor of coronary heart disease, commonly known as "vascular scavenger".

Figure 10:
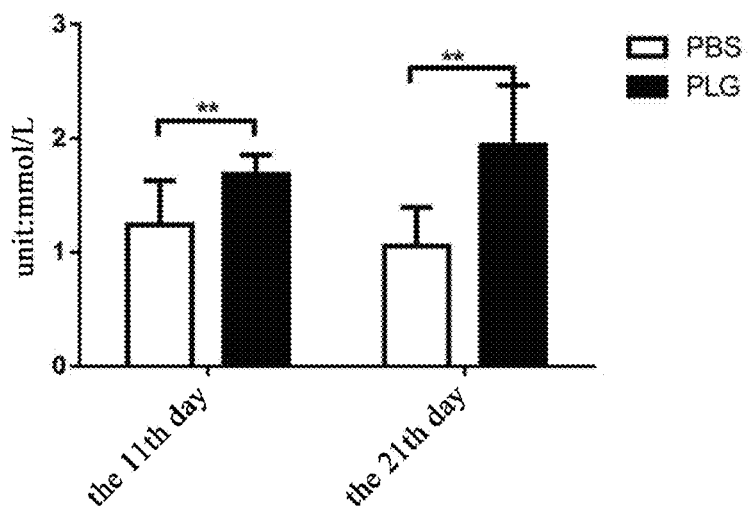
FIG. 10 shows detection results of serum high-density lipoprotein cholesterol after administration of plasminogen to 3% cholesterol hyperlipemia model mice for 10 days and 20 days. The results showed that the concentration of HDL-C in serum of mice in the group administered with plasminogen was remarkably higher than that in the control group administered with vehicle PBS, and the high-density lipoprotein concentrations of the two groups were statistically different after administration for 10 or 20 days (** indicates P<0.01). It indicates that plasminogen can effectively elevate the content of high-density lipoprotein cholesterol in serum of hyperlipemia model mice, and improve the dyslipidemia in hyperlipemia model mice.

The detection results showed that the concentration of HDL-C in serum of mice in the group administered with plasminogen was remarkably higher than that in the control group administered with vehicle PBS, and the HDL-C concentrations of the two groups were statistically different after administration for 10 or 20 days (FIG. 10). It indicates that plasminogen can elevate the content of high-density lipoprotein cholesterol in serum of hyperlipemia model mice, and improve the dyslipidemia in mice with hyperlipemia.

Example 11 Plasminogen Lowers the Serum Total Cholesterol Level in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with a 3% cholesterol high-fat diet. 50 μL of blood was taken from each mouse three days before administration, and the total cholesterol was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 20 days. On Day 20, the mice fasted for 16 hours, and on Day 21, 50 μL of blood was collected from orbital venous plexus, and centrifuged to obtain a supernatant. The total cholesterol was detected using a total cholesterol detection kit (Nanjing Jiancheng Bioengineering Institute, Cat #A111-1).

Figure 11:
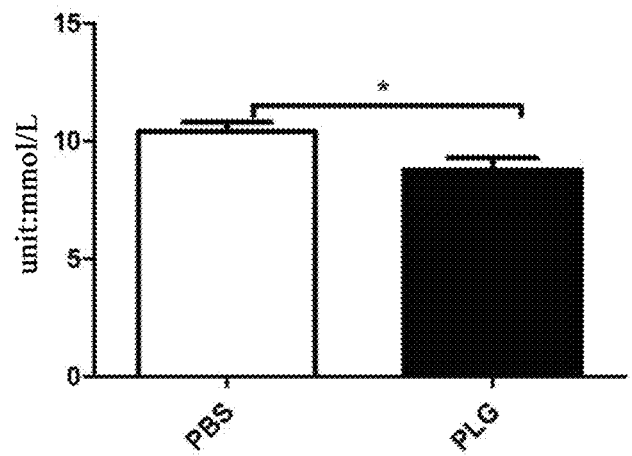
FIG. 11 shows detection results of serum total cholesterol after administration of plasminogen to 3% cholesterol hyperlipemia model mice for 20 days. The results showed that the concentration of total cholesterol in mice in the group administered with plasminogen was remarkably lower than that in the control group administered with vehicle PBS, and the statistical difference was significant (* indicates P<0.05). It indicates that plasminogen can lower the content of serum total cholesterol in hyperlipemia model mice, and has an effect of lowering blood lipid.

The detection results showed that the concentration of total cholesterol in mice in the group administered with plasminogen was remarkably lower than that in the control group administered with vehicle PBS, and the statistical difference was significant (FIG. 11). It indicates that plasminogen can lower the content of serum total cholesterol in hyperlipemia model mice.

Example 12 Plasminogen Lowers the Serum Low-Density Lipoprotein Cholesterol Level in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with a 3% cholesterol high-fat diet. 50 μL of blood was taken from each mouse three days before administration, and the total cholesterol was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 20 days.

On Day 20, the mice fasted for 16 hours, and on Day 21, 50 µL of blood was collected from orbital venous plexus, and centrifuged to obtain a supernatant. The low-density lipoprotein cholesterol (LDL-C) was detected using a low-density lipoprotein cholesterol detection kit (Nanjing Jiancheng Bioengineering Institute, Cat #A113-1).

Low-density lipoprotein is a lipoprotein particle that carries cholesterol into peripheral tissue cells and can be oxidized into oxidized low-density lipoprotein. When low-density lipoprotein, particularly oxidized low-density lipoprotein (OX-LDL) is in excess, the cholesterol it carries accumulates on the arterial wall, causing arteriosclerosis. Therefore, low-density lipoprotein cholesterol is called "bad cholesterol".

Figure 12:
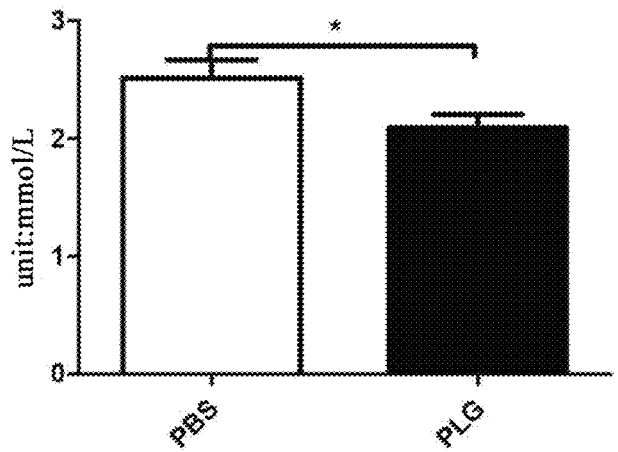
FIG. 12 shows detection results of serum low-density lipoprotein cholesterol after administration of plasminogen to 3% cholesterol hyperlipemia model mice for 20 days. The results showed that the concentration of LDL-C in mice in the group administered with plasminogen was remarkably lower than that in the control group administered with vehicle PBS, and the statistical difference was significant (* indicates P<0.05). It indicates that plasminogen can lower the content of low-density lipoprotein cholesterol in serum of hyperlipemia model mice, and has an effect of improving hyperlipemia.

The results showed that the concentration of LDL-C in mice in the group administered with plasminogen was remarkably lower than that in the control group administered with vehicle PBS, and the statistical difference was significant (FIG. 12). It indicates that plasminogen can reduce the content of low-density lipoprotein cholesterol in serum of hyperlipemia model mice, and improve the dyslipidemia in mice with hyperlipemia.

Example 13 Plasminogen Lowers Risk of Atherosclerosis Formation in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with a 3% cholesterol high-fat diet. 50 µL of blood was taken from each mouse three days before administration, and the total cholesterol (T-CHO) was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 µL of blood was collected from orbital venous plexus, and centrifuged to obtain a supernatant. The total cholesterol content was detected by using a total cholesterol detection kit (Nanjing Jiancheng Bioengineering Institute, Cat #A111-1); and the high-density lipoprotein cholesterol (HDL-C) content was detected using a high-density lipoprotein cholesterol detection kit (Nanjing Jiancheng Bioengineering Institute, Cat #A112-1).

Atherosclerosis index is a comprehensive index to predict atherosclerosis clinically. It is considered to be of greater clinical importance as an estimate of the risk of coronary heart disease than total cholesterol, triglyceride, high-density lipoprotein, and low-density lipoprotein alone [40]. Atherosclerosis index=(T-CHO-HDL-C)/HDL-C.

Figure 13:
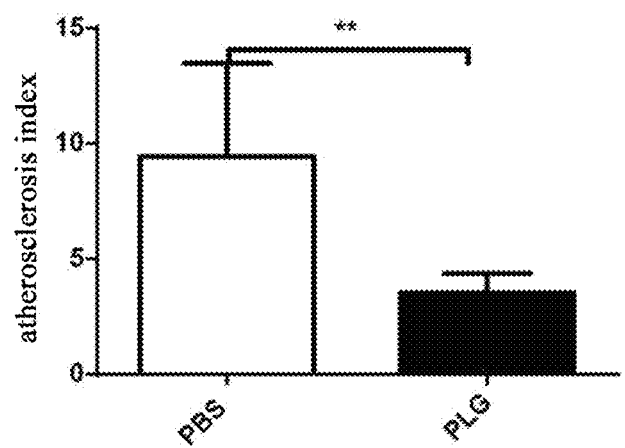
FIG. 13 shows detection results of serum atherosclerosis index after administration of plasminogen to 3% cholesterol hyperlipemia model mice for 20 days. The results showed that the atherosclerosis index of mice in the group administered with plasminogen was remarkably lower than that in the control group administered with vehicle PBS, and the statistical difference was extremely significant (** indicates P<0.01). It indicates that plasminogen can effectively lower the risk of atherosclerosis in hyperlipemia model mice.

The calculation results showed that the atherosclerosis index of mice in the group administered with plasminogen was remarkably lower than that in the control group administered with vehicle PBS, and the statistical difference was significant (FIG. 13). It indicates that plasminogen can lower the risk of atherosclerosis in hyperlipemia model mice.

Example 14 Plasminogen Lowers Risk of Onset of Heart Disease in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with a 3% cholesterol high-fat diet. 50 µL of blood was taken from each mouse three days before administration, and the total cholesterol (T-CHO) was detected. The mice were randomly divided into two groups based on the total cholesterol concentration, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 µL of blood was collected from orbital venous plexus, and centrifuged to obtain a supernatant. The total cholesterol content was detected by using a total cholesterol detection kit (Nanjing Jiancheng Bioengineering Institute, Cat #A111-1); and the high-density lipoprotein cholesterol (HDL-C) content was detected using a high-density lipoprotein cholesterol detection kit (Nanjing Jiancheng Bioengineering Institute, Cat #A112-1). Cardiac risk index=T-CHO/HDL-C.

Cardiac risk index (CRI) is used to assess the risk of heart disease induced by dyslipidemiar[40].

Figure 14:
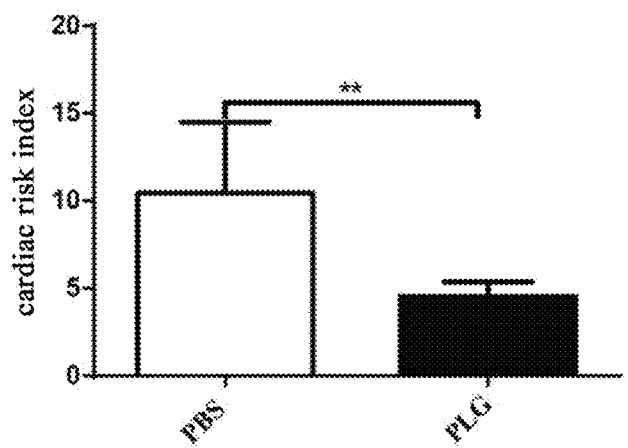
FIG. 14 shows results of serum cardiac risk index after administration of plasminogen to 3% cholesterol hyperlipemia model mice for 20 days. The results showed that CRI in the group administered with plasminogen was remarkably lower than that in the control group administered with vehicle PBS, and the statistical difference was extremely significant (** indicates P<0.01). It indicates that plasminogen can effectively lower the risk of heart disease in hyperlipemia model mice.

The results showed that CRI in the group administered with plasminogen was remarkably lower than that in the control group administered with vehicle PBS, and the statistical difference was extremely significant (FIG. 14). It indicates that plasminogen can effectively lower the risk of heart disease in hyperlipemia model mice.

Example 15 Plasminogen Alleviates Injury of Aortic Wall in Diabetic Mice

Figure 15:
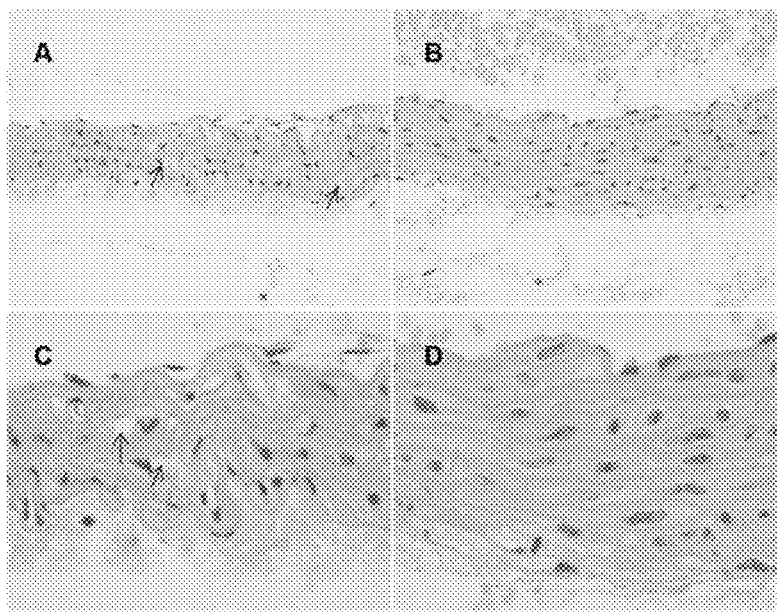
FIG. 15 shows an image of HE staining of aorta after administration of plasminogen to 24- to 25-week-old diabetic mice for 31 days. A and C refer to the control group administered with vehicle PBS, and B and D refer to the group administered with plasminogen. The results showed that in the control group administered with vehicle PBS, there was a foam cell deposition (indicated by arrow) on the vascular wall, the middle elastic membrane was arranged in disorder, and the vascular wall was thickened and accidented; while in the group administered with plasminogen, the middle elastic membrane had a regular structure in a wave shape, and the thickness of vascular wall was uniform. It indicates that the injection of plasminogen has a certain repair effect on aortic injury caused by diabetes mellitus.

Ten 24- to 25-week-old male db/db mice were randomly divided into two groups, five in the control group administered with vehicle PBS and five in the group administered with plasminogen, respectively. The mice were weighed and grouped on the day when the experiment began, i.e. Day 0. PBS or plasminogen was administered from day 1 for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein. Mice were sacrificed on Day 32, and the aortas were fixed in 10% neutral formalin fixative for 24 hours. The fixed aortas were paraffin-embedded after dehydration with alcohol gradient and permeabilization with xylene. The tissue sections were 5 µm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 400×(FIGS. 15A and B) and at 1000× (FIGS. 15C and D) oil immersion lens.

Diabetes mellitus with hyperlipemia is a common complication of diabetes mellitus and an important risk factor for diabetic macroangiopathy [41].

The staining results showed that in the control group administered with vehicle PBS (FIGS. 15A and C), there was a foam cell deposition (indicated by arrow) on the vascular wall, the middle elastic membrane was arranged in disorder, and the vascular wall was thickened and accidented; while in the group administered with plasminogen (FIGS. 15B and D), the middle elastic membrane has a regular structure in a wave shape, and the thickness of vascular wall was uniform. It indicates that the injection of plasminogen can reduce lipid deposition on the aortic wall of diabetic mice, and has a certain protective effect on the injury caused by lipid deposition on the arterial wall.

Example 16 Plasminogen Lowers Lipid Deposition in Ventricle of Diabetic Mice Nine 26-week-old male db/db mice were randomly divided into groups, 4 mice in the group administered with plasminogen, and 5 mice in the control group administered with vehicle PBS. Mice in the group administered with plasminogen were injected with human plasminogen at a dose of 2 mg/0.2 mL/mouse/day via the tail vein, and an equal volume of PBS was administered to mice in the control group administered with vehicle PBS via the tail vein, both lasting for 35 days. The mice were sacrificed on Day 36. The hearts were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 200×.

Figure 16:
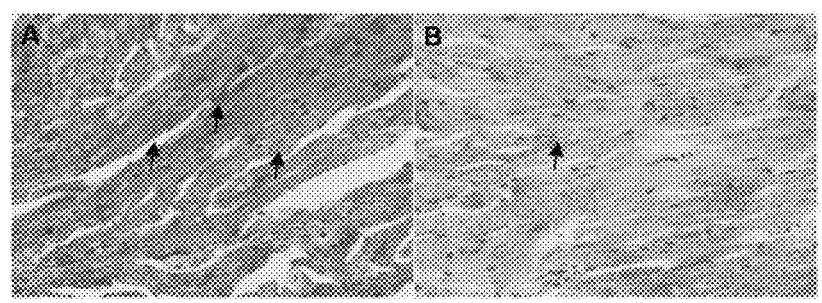
FIG. 16 shows a representative image of oil red O staining of ventricle after administration of plasminogen to 26-week-old diabetic mice for 35 days. A represents the control group administered with vehicle PBS, and B represents the group administered with plasminogen. The results showed that the lipid deposition in ventricle (indicated by arrow) of mice in the group administered with plasminogen was remarkably less than that in the control group administered with vehicle PBS. It indicates that plasminogen can reduce lipid deposition in ventricle of diabetic mice, and promote the repair of ventricular injury.

The results showed that the lipid deposition (indicated by arrow) in ventricle of mice in the group administered with plasminogen (FIG. 16B) was remarkably less than that in the control group administered with vehicle PBS (FIG. 16A). It indicates that plasminogen can reduce fat deposition in ventricle of diabetic mice, and promote the repair of ventricular injury.

Example 17 Plasminogen Increases the High-Density Lipoprotein Cholesterol Level in Serum of Diabetic Mice Twenty 26-week-old male db/db mice were randomly divided into groups, 11 mice in the group administered with plasminogen, and 9 mice in the control group administered with vehicle PBS. The mice were weighed and grouped on the day when the experiment began, i.e. Day 0. Plasminogen or PBS was administered from day 1 for 35 consecutive days. Mice in the group administered with plasminogen were injected with human plasminogen at a dose of 2 mg/0.2 mL/mouse/day via the tail vein, and an equal volume of PBS was administered to mice in the control group via the tail vein. On Day 36, the whole blood was collected from removed eyeballs in mice, and centrifuged at 3500 r/min at 4° C. for 10 min to obtain a supernatant, which was detected for the concentration of high-density lipoprotein cholesterol (HDL-C) in serum using a high-density lipoprotein detection kit (Nanjing Jiancheng Bioengineering Institute, Cat #A112-1).

Figure 17:
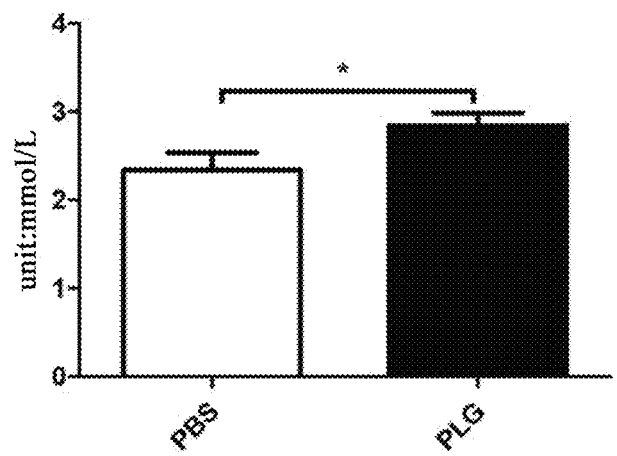
FIG. 17 shows detection results of the content of high-density lipoprotein cholesterol in serum after administration of plasminogen to 26-week-old diabetic mice for 35 days. The results showed that after 35 days of continuous injection of human plasminogen into diabetic mice, the content of HDL-C in serum of mice in the group administered with plasminogen was higher than that in the control group administered with vehicle PBS, and the statistical difference was significant. It indicates that the injection of plasminogen can promote the increase in the content of serum high-density lipoprotein cholesterol, and improve the dyslipidemia in diabetic mice.

The detection results showed that the content of HDL-C in serum of mice in the group administered with plasminogen was higher than that in the control group administered with vehicle PBS, and the statistical difference was significant (FIG. 17). It indicates that the injection of plasminogen can promote the increase in the content of serum high-density lipoprotein cholesterol, and improve the dyslipidemia of diabetes mellitus.

Example 18 Plasminogen Lowers Low-Density Lipoprotein Cholesterol in Serum of Diabetic Mice Ten 24- to 25-week-old male db/db mice were randomly grouped, 5 mice in each of the group administered with plasminogen and the control group administered with vehicle PBS. Three db/m mice were taken as the normal control group. The mice were weighed and grouped on the day when the experiment began, i.e. Day 0. Plasminogen or PBS was administered from day 1 for 31 consecutive days. Mice in the group administered with plasminogen were injected with human plasminogen at a dose of 2 mg/0.2 mL/mouse/day via the tail vein, an equal volume of PBS was administered to mice in the PBS control group via the tail vein, and mice in the normal control group received no treatment. On Day 32, the whole blood was collected from removed eyeballs in mice, and centrifuged at 3500 r/min at 4° C. for 10 min to obtain a supernatant, which was detected for the concentration of low-density lipoprotein cholesterol (LDL-C) in serum using a low-density lipoprotein cholesterol detection kit (Nanjing Jiancheng Bioengineering Institute, Cat #A113-1).

Figure 18:
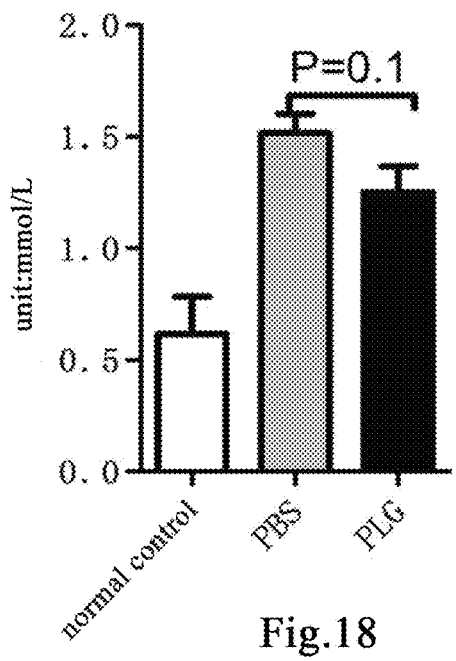
FIG. 18 shows detection results of the content of low-density lipoprotein cholesterol (LDL-C) in serum after administration of plasminogen to 24- to 25-week-old diabetic mice for 31 days. The results showed that after continuous injection of human plasminogen into diabetic model mice for 31 days, the content of LDL-C in serum of mice in the group administered with plasminogen was lower than that in the control group administered with vehicle PBS, and the statistical difference was close to significant (P=0.1). It indicates that plasminogen can lower the content of low-density lipoprotein cholesterol in serum of diabetic mice.

The results showed that after continuous injection of human plasminogen into diabetic model mice for 31 days, the content of LDL-C in serum of mice in the group administered with plasminogen was lower than that in the control group administered with vehicle PBS, and the statistical difference was close to significant (P=0.1) (FIG. 18). It indicates that plasminogen can lower the content of LDL-C in serum.

Example 19 Plasminogen Lowers the Content of Serum Total Cholesterol in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [30,31]. The model mice continued to be fed with a high-fat and high-cholesterol diet. 50 μL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for the total cholesterol using a total cholesterol detection kit (Nanjing Jiancheng Bioengineering Institute, Cat #A111-1).

Figure 19:
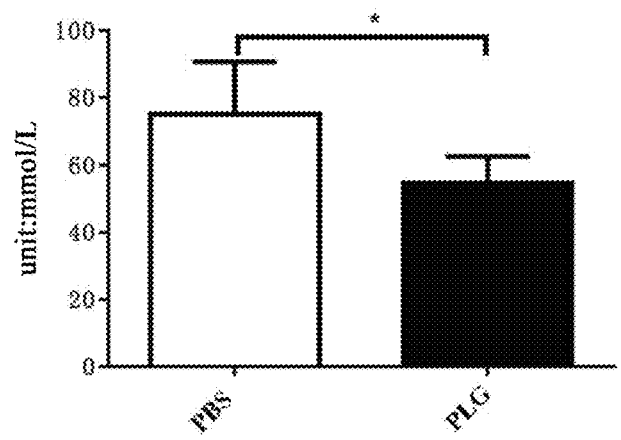
FIG. 19 shows detection results of serum total cholesterol after administration of plasminogen to ApoE atherosclerosis model mice for 30 days. The results showed that the concentration of total cholesterol in mice in the group administered with plasminogen was remarkably lower than that in the control group administered with vehicle PBS, and the statistical difference was significant (* indicates P<0.05). It indicates that plasminogen can lower the content of total cholesterol in serum of ApoE atherosclerosis model mice, and improve the dyslipidemia in atherosclerosis model mice.

The detection results showed that the concentration of total cholesterol in mice in the group administered with plasminogen was remarkably lower than that in the control group administered with vehicle PBS, and the statistical difference was significant (P=0.014) (FIG. 19). It indicates that plasminogen can lower the content of total cholesterol in serum of ApoE atherosclerosis model mice, and improve the dyslipidemia of atherosclerosis.

Example 20 Plasminogen Lowers the Content of Serum Triglyceride in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [30,31]. The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for triglyceride using a triglyceride detection kit (Nanjing Jiancheng Bioengineering Institute, Cat #A110-1).

Figure 20:
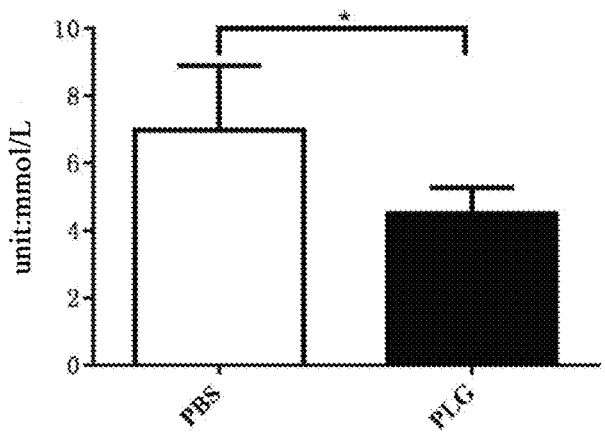
FIG. 20 shows detection results of serum triglyceride after administration of plasminogen to ApoE atherosclerosis model mice for 30 days. The results showed that the concentration of triglyceride in mice in the group administered with plasminogen was remarkably lower than that in the control group administered with vehicle PBS, and the statistical difference was significant (* indicates P<0.05). It indicates that plasminogen can lower the content of triglyceride in serum of ApoE atherosclerosis model mice, and improve the dyslipidemia in atherosclerosis model mice.

The detection results showed that the concentration of triglyceride in mice in the group administered with plasminogen was remarkably lower than that in the control group administered with vehicle PBS, and the statistical difference was significant (P=0.013) (FIG. 20). It indicates that plasminogen can lower the content of triglyceride in serum of ApoE atherosclerosis model mice, and improve the dyslipidemia of atherosclerosis.

Example 21 Plasminogen Lowers the Content of Serum Low-Density Lipoprotein Cholesterol in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [30,31]. The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for LDL-C using a low-density lipoprotein cholesterol (LDL-C) detection kit (Nanjing Jiancheng Bioengineering Institute, Cat #A113-1).

Figure 21:
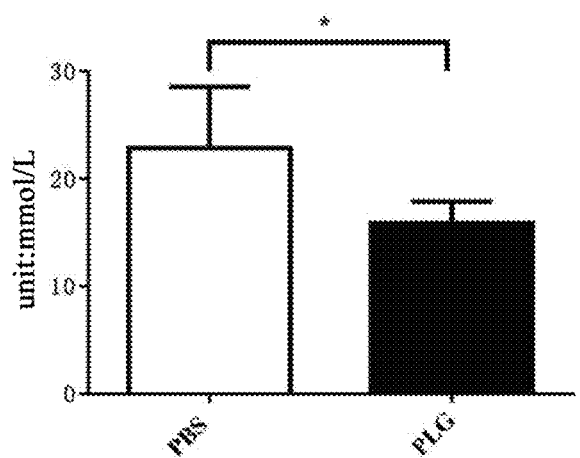
FIG. 21 shows detection results of serum low-density lipoprotein cholesterol after administration of plasminogen to ApoE atherosclerosis model mice for 30 days. The results showed that the concentration of LDL-C in mice in the group administered with plasminogen was remarkably lower than that in the control group administered with vehicle PBS, and the statistical difference was significant (* indicates P<0.05). It indicates that plasminogen can lower the content of low-density lipoprotein cholesterol in serum of ApoE atherosclerosis model mice, and improve the dyslipidemia in atherosclerosis model mice.

The results showed that the concentration of LDL-C in mice in the group administered with plasminogen was remarkably lower than that in the control group administered with vehicle PBS, and the statistical difference was significant (P=0.017) (FIG. 21). It indicates that plasminogen can lower the content of low-density lipoprotein cholesterol in serum of ApoE atherosclerosis model mice, and improve the dyslipidemia in atherosclerosis model mice.

Example 22 Plasminogen Ameliorates Lipid Deposition in Aortic Sinus of ApoE Atherosclerosis Mice Thirteen 6-week-old male ApoE mice were fed with a high-fat and high-cholesterol diet (Nantong TROPHIC, TP2031) for 16 weeks to induce the atherosclerosis model [30,31]. The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. The mice were sacrificed on Day 31. The heart tissues were fixed in 4% paraformaldehyde for 24 to 48 hours, then sedimented in 15% and 30% sucrose at 4° C. overnight, respectively, and embedded in OCT. The frozen sections were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 40×.

Figure 22:
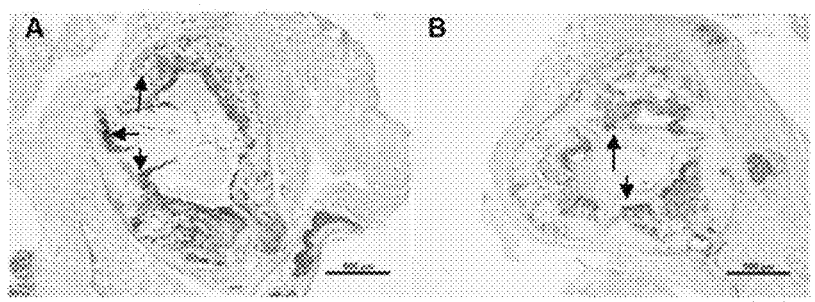
FIG. 22 shows a representative image of oil red O staining of aortic sinus after administration of plasminogen to ApoE atherosclerosis model mice for 30 days. A represents the control group administered with vehicle PBS, and B represents the group administered with plasminogen. The results showed that the fat deposition in aortic sinus of mice in the group administered with plasminogen was remarkably lower than that in the control group administered with vehicle PBS. It indicates that plasminogen can ameliorate fat deposition in aortic sinus of atherosclerosis model mice.

The staining results showed that the fat deposition in aortic sinus of mice in the group administered with plasminogen (FIG. 22B) was remarkably lower than that in the control group administered with vehicle PBS (FIG. 22A). It indicates that plasminogen can reduce lipid deposition in aortic sinus of atherosclerosis model mice.

Figure 23:
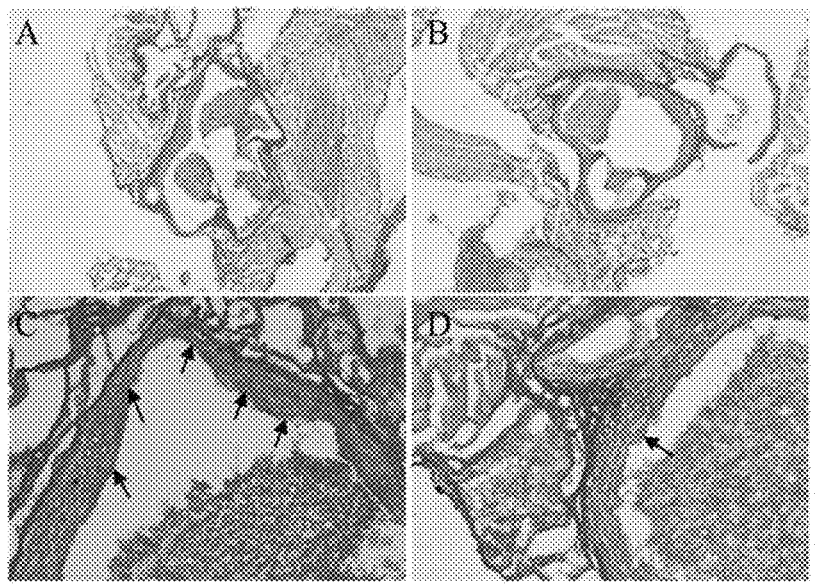
FIG. 23 shows a representative image of Sirius red staining of aortic sinus after administration of plasminogen to 16-week hyperlipemia model mice for 30 days. A and C refer to the control group administered with vehicle PBS, and B and D refer to the group administered with plasminogen. The results showed that the area of collagen deposition (indicated by arrow) on the inner walls of blood vessels of aortic sinus in the group administered with plasminogen was remarkably less than that in the control group administered with vehicle PBS, indicating that plasminogen can alleviate the level of aortic sinus fibrosis in hyperlipemia model mice.

Example 23 Plasminogen Reduces Aortic Sinus Fibrosis in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [32,33]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours. The fixed tissues were paraffin-embedded after dehydration with alcohol gradient and permeabilization with xylene. The aortic sinus sections was 3 µm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 40×(FIGS. 23A and 23B) and 200×(FIGS. 23C and 23D).

The results showed that the area of collagen deposition (indicated by arrow) on the inner walls of blood vessels of aortic sinus in the group administered with plasminogen (FIGS. 23B and 23D) was remarkably less than that in the control group administered with vehicle PBS (FIGS. 23A and 23C), indicating that plasminogen can alleviate the level of aortic sinus fibrosis in hyperlipemia model mice.

Example 24 Plasminogen Ameliorates Compensatory Cardiac Hypertrophy in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [47,48]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. After weighed on Day 31 of administration, the mice were sacrificed, their hearts were weighed, and cardiac coefficients were calculated. Cardiac coefficient (%)=heart weight/body weight× 100.

Figure 24:
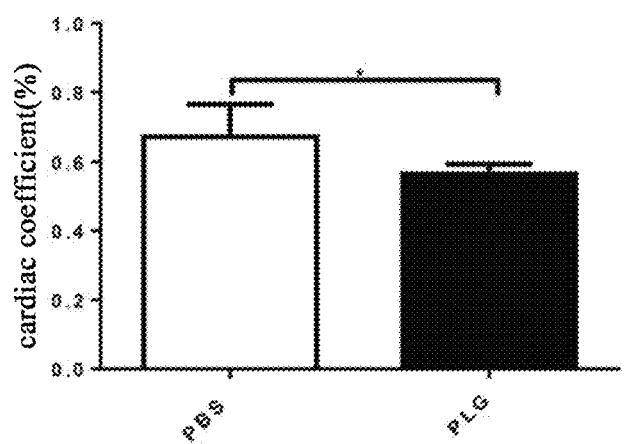
FIG. 24 shows statistical results of cardiac coefficient after administration of plasminogen to ApoE atherosclerosis model mice for 30 days. The results showed that the cardiac organ coefficient of mice in the group administered with plasminogen was remarkably lower than that in the control group administered with vehicle PBS. It indicates that plasminogen can ameliorate the compensatory cardiac hypertrophy caused by cardiac injury in ApoE atherosclerosis model mice.

The results showed that the cardiac coefficient of mice in the group administered with plasminogen was remarkably lower than that in the control group administered with vehicle PBS (FIG. 24). It indicates that plasminogen can alleviate the compensatory cardiac hypertrophy caused by cardiac injury in ApoE atherosclerosis model mice.

Example 25 Plasminogen Lowers Renal Fibrosis in 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with the 3% cholesterol high-fat diet. Another five male C57 mice of the same week age were taken as the blank control group, and were fed with a normal maintenance diet during the experiment. 50 µL of blood was taken from each mouse three days before administration, and the total cholesterol was detected. The model mice were randomly divided into two groups based on the total cholesterol concentration and the body weight, i.e., the group administered with plasminogen, and the control group administered with vehicle PBS, 8 mice in each group. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for a period of 30 days and sacrificed on Day 31. The kidneys were fixed in 4% paraformaldehyde for 24 to 48 hours. The fixed tissues were paraffin-embedded after dehydration with alcohol gradient and permeabilization with xylene. The kidney tissue sections was 3 µm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 25:
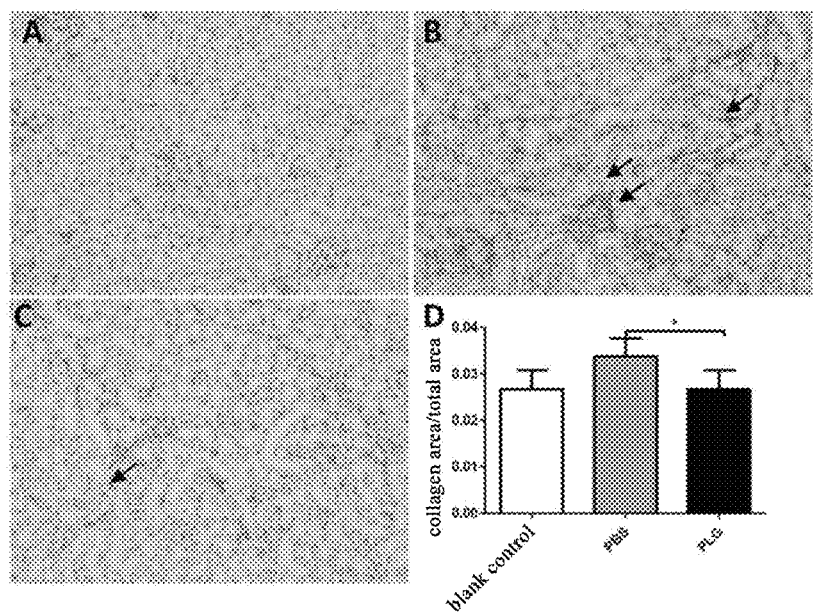
FIG. 25 shows observed results of Sirius red staining of kidney after administration of plasminogen to 3% cholesterol hyperlipemia model mice for 30 days. A represents the blank control group, B represents the control group administered with vehicle PBS, C represents the group administered with plasminogen, and D represents the quantitative analysis results. The results showed that the collagen deposition in kidney (indicated by arrow) in the group administered with plasminogen was remarkably less than that in the control group administered with vehicle PBS, and the statistical difference was significant; and in the group administered with plasminogen, fibrosis was substantially restored to a normal level. It indicates that plasminogen can effectively reduce renal fibrosis in 3% cholesterol hyperlipemia model mice.

The results showed that the collagen deposition in kidney (indicated by arrow) in the group administered with plasminogen (FIG. 25C) was remarkably less than that in the control group administered with vehicle PBS (FIG. 25B), and the statistical difference was significant (FIG. 25D); while in the group administered with plasminogen, fibrosis was substantially restored to a normal level (FIG. 25A). It indicates that plasminogen can effectively reduce renal fibrosis in 3% cholesterol hyperlipemia model mice.

Example 26 Plasminogen Lowers Fat Deposition in Kidney of 3% Cholesterol Hyperlipemia Model Mice Sixteen 9-week-old male C57 mice were fed with a 3% cholesterol high-fat diet (Nantong TROPHIC) for 4 weeks to induce hyperlipemia [32,33]. This model was designated as the 3% cholesterol hyperlipemia model. The model mice continued to be fed with the 3% cholesterol high-fat diet. Another five male C57 mice of the same week age were taken as the blank control group, and were fed with a normal maintenance diet during the experiment. 50 µL of blood was taken from each mouse three days before administration, and the total cholesterol was detected. The model mice were randomly divided into two groups based on the total cholesterol concentration and the body weight, i.e., the group administered with plasminogen, and the control group administered with vehicle PBS, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. The mice were sacrificed on Day 31. The kidneys were fixed in 4% paraformaldehyde for 24 to 48 hours, then sedimented in 15% and 30% sucrose at 4° C. overnight, respectively, and embedded in OCT. The frozen sections were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 400×.

Figure 26:
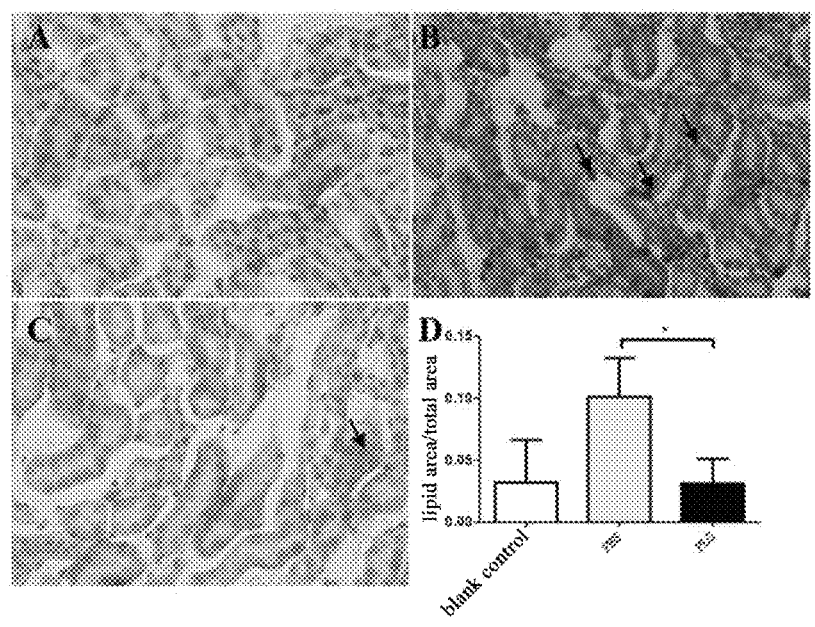
FIG. 26 shows observed results of oil red O of kidney after administration of plasminogen to 3% cholesterol hyperlipemia model mice for 30 days. A represents the blank control group, B represents the control group administered with vehicle PBS, C represents the group administered with plasminogen, and D represents the quantitative analysis results. The results showed that the fat deposition in kidney (indicated by arrow) of mice in the group administered with plasminogen was remarkably less than that in the control group administered with vehicle PBS, and the quantitative analysis showed significant statistical difference; in addition, the lipid deposition level in the group administered with plasminogen was similar to that in mice in the blank control group. It indicates that plasminogen can reduce the fat deposition in kidney of hyperlipemia model mice, and thus reduce renal injury caused by fat deposition.

The results showed that the fat deposition in kidney (indicated by arrow) of mice in the group administered with plasminogen (FIG. 26C) was remarkably less than that in the control group administered with vehicle PBS (FIG. 26B), and the quantitative analysis showed significant statistical difference (FIG. 26D); in addition, the lipid deposition level in the group administered with plasminogen was similar to that in mice in the blank control group (FIG. 26A). It indicates that plasminogen can reduce the fat deposition in kidney of hyperlipemia model mice, and thus reduce renal injury caused by fat deposition.

REFERENCES

[1] Edited by Zhao Kejian. Manual of Modern Pharmic Terms. Beijing: China Medical Science Press. 2004. page 533

[2] Shafrir E., Raz. I. Diabetes: Mellitus or Lipidus [J]. Diabetologia, 2003, 46:433-440.

[3] Mooradian A D. Cardiovascular disease in type 2 diabetes mellitus: Current management guidelines [J]. Arch Intern Med. 2003, 163:33-40.

[4] Appel G. Lipid adnormalities in renal disease [J]. Kidney Int, 1991, 39:169.

[5] J Zah, Kov, H Varerkov, et al., Dislipoproteinemia and Chronic Kidney Failure [J]. VnitrLek. 2000, 46(9):539-46.

[6] EffatRazeghi, Mohammadreza Shafipour et al. Lipid Disturbances Before and After Renal Transplant. EffatRazeghi et al/Experimental and Clinical Transplantation (2011) 4: 230-235

[7] Grone H J. Glomerular lipids in non-hereditary forms of glomerulopathy/glomerulo nephritis [J]. Nephrol. Dial Transplant. 1999, 14:1595-1598.

[8] Larking R C. Dunlop M E, The link between hyperglycaemia and diabetic nephropathy [J] Athrosclerosis, 2001, 156(2):25-33.

[9] Alexander C M and Werb, Z. (1991). Extracellular matrix degradation. In Cell Biology of Extracellular Matrix, Hay E D, ed. (New York: Plenum Press), pp. 255-302.

[10] Werb, Z., Mainardi, C. L., Vater, C. A., and Harris, E. D., Jr. (1977). Endogenous activation of latent collagenase by rheumatoid synovial cells. Evidence for a role of plasminogen activator. N. Engl. J. Med. 296, 1017-1023.

[11] He, C. S., Wilhelm, S. M., Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad. Sci. U.S.A 86, 2632-2636.

[12] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.

[13] Vassalli, J. D., Baccino, D., and Belin, D. (1985). A cellular binding site for the Mr 55, 000 form of the human plasminogen activator, urokinase. J. Cell Biol. 100, 86-92.

[14] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[15] Saksela, O. and Rifkin, D. B. (1988). Cell-associated plasminogen activation: regulation and physiological functions. Annu. Rev. Cell Biol. 4, 93-126.

[16] Raum, D., Marcus, D., Alper, C. A., Levey, R., Taylor, P. D., and Starzl, T. E. (1980). Synthesis of human plasminogen by the liver. Science 208, 1036-1037.

[17] Wallén P (1980). Biochemistry of plasminogen. In Fibrinolysis, Kline D L and Reddy K K N, eds. (Florida: CRC)

[18] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.

[19] Collen, D. and Lijnen, H. R. (1991). Basic and clinical aspects of fibrinolysis and thrombolysis. Blood 78, 3114-3124.

[20] Alexander, C. M. and Werb, Z. (1989). Proteinases and extracellular matrix remodeling. Curr. Opin. Cell Biol. 1, 974-982.

[21] Mignatti, P. and Rifkin, D. B. (1993). Biology and biochemistry of proteinases in tumor invasion. Physiol Rev. 73, 161-195.

[22] Collen, D. (2001). Ham-Wasserman lecture: role of the plasminogen system in fibrin-homeostasis and tissue remodeling. Hematology. (Am. Soc. Hematol. Educ. Program.) 1-9.

[23] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[24] Andreasen, P. A., Kjoller, L., Christensen, L., and Duffy, M. J. (1997). The urokinase-type plasminogen activator system in cancer metastasis: a review. Int. J. Cancer 72, 1-22.

[25] Rifkin, D. B., Mazzieri, R., Munger, J. S., Noguera, I., and Sung, J. (1999). Proteolytic control of growth factor availability. APMIS 107, 80-85.

[26] Marder V J, Novokhatny V. Direct fibrinolytic agents: biochemical attributes, preclinical foundation and clinical potential [J]. Journal of Thrombosis and Haemostasis, 2010, 8(3): 433-444.

[27] Hunt J A, Petteway Jr S R, Scuderi P, et al. Simplified recombinant plasmin: production and functional comparison of a novel thrombolytic molecule with plasma-derived plasmin [J]. ThrombHaemost, 2008, 100(3): 413-419.

[28] Sottrup-Jensen L, Claeys H, Zajdel M, et al. The primary structure of human plasminogen: Isolation of two lysine-binding fragments and one "mini"-plasminogen (MW, 38, 000) by elastase-catalyzed-specific limited proteolysis [J]. Progress in chemical fibrinolysis and thrombolysis, 1978, 3: 191-209.

[29] Nagai N, Demarsin E, Van Hoef B, et al. Recombinant human microplasmin: production and potential therapeutic properties [J]. Journal of Thrombosis and Haemostasis, 2003, 1(2): 307-313.

[30] Yutaka Nakashima, Andrew S. Plump, Elaine W. Raines et al. ArteriosclerThromb. 1994 January; 14(1):133-40.

[31] Yvonne Nitschke, Gabriele Weissen-Plenz, Robert Terkeltaub et al. Nppl promotes atherosclerosis in ApoE knockout mice. J. Cell. Mol. Med. Vol 15, No 11, 2011 pp. 2273-2283.

[32] Dominika Nackiewicz, Paromita Dey, Barbara Szczerba et al. Inhibitor of differentiation 3, a transcription factor regulates hyperlipidemia associated kidney disease. Nephron Exp Nephrol. 2014; 126(3): 141-147.

[33] Ming Gul, Yu Zhang., Shengjie Fan et al. Extracts of RhizomaPolygonatiOdorati Prevent High-Fat Diet-Induced Metabolic Disorders in C57BL/6 Mice. PLoS ONE 8(11): e81724.

[34] Siobhan M. Craige, PhD, Shashi Kant et al. Endothelial NADPH oxidase 4 protects ApoE−/− mice from atherosclerotic lesions. Free RadicBiol Med. 2015 December; 89: 1-7.

[35] Dimitrios Davalos, Katerina Akassoglou. Fibrinogen as a key regulator of inflammation in disease. Seminars in Immunopathology, 2012. 34(1):43-62.

[36] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

[37] Zhang M, Takahashi K, Alicot E M, Vorup-Jensen T, Kessler B, et al. (2006) Activation of the lectin pathway by natural IgM in a model of ischemia reperfusion injury. J Immunol 177: 4727-4734.

[38] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

[39] R. Langhorn and J. L. Willesen. Cardiac Troponins in Dogs and Cats. J Vet Intern Med 2016; 30:36-50.

[40] Sungwon Lee, Youngjoo Lee, Jiyeon Kim et al. Atorvastatin and rosuvastatin improve physiological param-eters and alleviate immune dysfunction in metabolic disorders. BiochemBiophys Res Commun. 2016 Sep. 23; 478(3): 1242-7.

[41] Ametov A S, KulidzhanianNK.Diabetes mellitus is an independent risk factor for cardiovascular disease. Ter Arkh. 2012; 84(8):91-4.

The invention claimed is:

1. A method for treating fatty liver in a subject, comprising administering a prophylactically and/or therapeutically effective amount of plasminogen to the subject, wherein the subject suffers from fatty liver, wherein plasminogen comprises an amino acid sequence of at least 75% sequence identity with SEQ ID NO: 2 and has the plasminogen activity, and wherein the plasminogen comprise an amino acid sequence of at least 80% identity to SEQ ID NO: 14 and has serine protease activity.

2. The method of claim 1, wherein the fatty liver comprises obesity-induced fatty liver, alcohol-induced fatty liver, rapid weight loss induced fatty liver, malnutrition-induced fatty liver, diabetic fatty liver, or drug-induced fatty liver.

3. The method of claim 1, wherein the fatty liver is elicited or accompanied by a disease or condition selected from the group consisting of an endocrine disorder disease, a glucose metabolism disease, a liver disease, a kidney disease, a cardiovascular disease, an intestinal disease, a thyroid disease, a gallbladder or a biliary tract disease, obesity, drinking, and a drug therapy.

4. The method of claim 3, wherein the fatty liver is elicited or accompanied by a disease selected from the group consisting of hypertension, diabetes mellitus, chronic hepatitis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and an oestrogen therapy.

5. A method for treating lipid deposition in liver in a subject, comprising administering a prophylactically and/or therapeutically effective amount of plasminogen to the subject, wherein the subject suffers from, lipid deposition in liver, wherein plasminogen comprises an amino acid sequence of at least 75% sequence identity with SEQ ID NO: 2 and has the plasminogen activity, and wherein the plasminogen comprise an amino acid sequence of at least 80% identity to SEQ ID NO: 14 and has serine protease activity.

6. The method of claim 5, wherein the lipid deposition in liver is elicited or accompanied by a disease or condition selected from the group consisting of an endocrine disorder disease, a glucose metabolism disease, a liver disease, a kidney disease, a cardiovascular disease, an intestinal disease, a thyroid disease, a gallbladder or a biliary tract disease, obesity, drinking, and a drug therapy.

7. The method of claim 6, wherein the lipid deposition in liver is elicited or accompanied by a disease selected from the group consisting of hypertension, atherosclerosis, hyperlipemia, diabetes mellitus, chronic hepatitis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and a drug therapy.

8. The method of claim 7, wherein the lipid deposition in liver is accompanied by hyperlipemia, and wherein the hyperlipemia exhibits one or more selected from: elevated serum triglyceride (TG), elevated serum low-density lipoprotein (LDL), and elevated very low-density lipoprotein (VLDL).

9. The method of claim 7, wherein the lipid deposition in liver is accompanied by hyperlipemia, and wherein the hyperlipemia comprises hypercholesterolemia, hypertriglyceridemia, combined hyperlipemia, or hypo-high-density lipoproteinemia.

10. The method of claim 1, wherein the plasminogen is administered in combination with one or more other drugs or therapies.

11. The method of claim 10, wherein the one or more other drugs or therapies comprises a drug for treating diabetes mellitus, a drug for treating atherosclerosis, a drug for treating nephrotic syndrome, a drug for treating renal insufficiency, a drug for treating uremia, a drug for treating kidney transplantation, a drug for treating fatty liver, a drug for treating hepatic cirrhosis, or a drug for treating obesity.

12. The method of claim 11, wherein the one or more other drugs or therapies comprises: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, or thyroxine.

13. The method of claim 1, wherein the plasminogen is selected from Glu-plasminogen, Lys-plasminogen, mini-plasminogen, micro-plasminogen, delta-plasminogen and variants thereof that retain the plasminogen activity.

14. The method of claim 1, wherein the plasminogen is a natural or synthetic human plasminogen, or a variant or fragment thereof that still retains the plasminogen activity.

15. The method of claim 1, wherein the plasminogen is administered to the subject at a dosage of 1-100 mg/kg at a frequency of weekly to daily.

16. The method of claim 15, wherein the plasminogen is administered at least daily.

17. The method of claim 1, wherein the method ameliorates fat deposition in liver, lipid deposition in aortic sinus, collagen deposition in heart, and/or renal fibrosis.

* * * * *

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen (Glu-PLG,Glu-plasminogen)without the signal peptide

<400> SEQUENCE: 1
gagcctctgg atgactatgt gaatacccag ggggcttcac tgttcagtgt cactaagaag       60
cagctgggag caggaagtat agaagaatgt gcagcaaaat gtgaggagga cgaagaattc      120
acctgcaggg cattccaata tcacagtaaa gagcaacaat gtgtgataat ggctgaaaac      180
aggaagtcct ccataatcat taggatgaga gatgtagttt tatttgaaaa gaaagtgtat      240
ctctcagagt gcaagactgg gaatggaaag aactacagag gacgatgtc caaaacaaaa       300 aatggcatca cctgtcaaaa atggagttcc acttctcccc acagacctag attctcacct      360
gctacacacc cctcagaggg actggaggag aactactgca ggaatccaga caacgatccg      420
caggggccct ggtgctatac tactgatcca gaaaagagat atgactactg cgacattctt      480
gagtgtgaag aggaatgtat gcattgcagt ggagaaaact atgacggcaa aatttccaag      540
accatgtctg gactggaatg ccaggcctgg gactctcaga gcccacacgc tcatggatac      600
attccttcca aatttccaaa caagaacctg aagaagaatt actgtcgtaa ccccgatagg      660
gagctgcggc cttggtgttt caccaccgac cccaacaagc gctgggaact tgtgacatc      720 ccccgctgca aacacctcc accatcttct ggtcccacct accagtgtct gaagggaaca      780
ggtgaaaact atcgcgggaa tgtggctgtt accgtgtccg ggcacacctg tcagcactgg      840
agtgcacaga cccctcacac acataacagg acaccagaaa acttcccctg caaaaatttg      900
gatgaaaact actgccgcaa tcctgacgga aaagggccc catggtgcca tacaaccaac      960
agccaagtgc ggtgggagta ctgtaagata ccgtcctgtg actcctcccc agtatccacg     1020
gaacaattgg ctcccacagc accacctgag ctaaccctg tggtccagga ctgctaccat     1080
ggtgatggac agagctaccg aggcacatcc tccaccacca ccacaggaaa gaagtgtcag     1140
tcttggtcat ctatgacacc acaccggcac cagaagaccc cagaaaacta cccaaatgct     1200
ggcctgacaa tgaactactg caggaatcca gatgccgata aggccctg gtgttttacc      1260 acagacccca gcgtcaggtg ggagtactgc aacctgaaaa aatgctcagg aacagaagcg     1320
agtgttgtag cacctccgcc tgttgtcctg cttccagatg tagagactcc ttccgaagaa     1380
gactgtatgt ttgggaatgg gaaaggatac cgaggcaaga gggcgaccac tgttactggg     1440
acgccatgcc aggactgggc tgcccaggag ccccatagac acagcatttt cactccagag     1500
acaaatccac gggcgggtct ggaaaaaaat tactgccgta accctgatgg tgatgtaggt     1560
ggtccctggt gctacacgac aaatccaaga aaactttacg actactgtga tgtccctcag     1620
tgtgcggccc cttcatttga ttgtgggaag cctcaagtgg agccgaagaa atgtcctgga     1680
agggttgtag gggggtgtgt ggcccaccca cattcctggc cctggcaagt cagtcttaga     1740
```

```
acaaggtttg gaatgcactt ctgtggaggc accttgatat ccccagagtg ggtgttgact    1800
gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccagggtgac    2220
agtggaggtc ctctggtttg cttcgagaag gacaaataca ttttacaagg agtcacttct    2280
tggggtcttg gctgtgcacg cccaataag cctggtgtct atgttcgtgt ttcaaggttt    2340
gttacttgga ttgagggagt gatgagaaat aattaa                             2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240
```

```
Pro Arg Cys Thr Thr Pro Pro Ser Ser Gly Pro Thr Tyr Gln Cys
            245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
            645                 650                 655

Val Ile Thr Asp Lys Val Ile Pro Ala Cys Leu Pro Ser Pro Asn Tyr
```

```
              660             665             670
Val Val Ala Asp Arg Thr Glu Cys Phe Ile Thr Gly Trp Gly Glu Thr
            675                 680                 685
Gln Gly Thr Phe Gly Ala Gly Leu Leu Lys Glu Ala Gln Leu Pro Val
        690                 695                 700
Ile Glu Asn Lys Val Cys Asn Arg Tyr Glu Phe Leu Asn Gly Arg Val
705                 710                 715                 720
Gln Ser Thr Glu Leu Cys Ala Gly His Leu Ala Gly Gly Thr Asp Ser
                725                 730                 735
Cys Gln Gly Asp Ser Gly Gly Pro Leu Val Cys Phe Glu Lys Asp Lys
            740                 745                 750
Tyr Ile Leu Gln Gly Val Thr Ser Trp Gly Leu Gly Cys Ala Arg Pro
        755                 760                 765
Asn Lys Pro Gly Val Tyr Val Arg Val Ser Arg Phe Val Thr Trp Ile
        770                 775                 780
Glu Gly Val Met Arg Asn Asn
785                 790
```

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural plasminogen (from swiss prot)with the signal peptide

<400> SEQUENCE: 3

| | | | | | |
|---|---|---|---|---|---|
| atggaacata | aggaagtggt | tcttctactt | cttttatttc | tgaaatcagg | tcaaggagag | 60 |
| cctctggatg | actatgtgaa | tacccagggg | gcttcactgt | tcagtgtcac | taagaagcag | 120 |
| ctgggagcag | gaagtataga | agaatgtgca | gcaaaatgtg | aggaggacga | agaattcacc | 180 |
| tgcagggcat | tccaatatca | cagtaaagag | caacaatgtg | tgataatggc | tgaaaacagg | 240 |
| aagtcctcca | taatcattag | gatgagagat | gtagttttat | ttgaaaagaa | agtgtatctc | 300 |
| tcagagtgca | agactgggaa | tggaaagaac | tacagaggga | cgatgtccaa | aacaaaaaat | 360 |
| ggcatcacct | gtcaaaaatg | gagttccact | tctcccccaca | gacctagatt | ctcacctgct | 420 |
| acacacccct | cagagggact | ggaggagaac | tactgcagga | atccagacaa | cgatccgcag | 480 |
| gggccctggt | gctatactac | tgatccagaa | aagagatatg | actactgcga | cattcttgag | 540 |
| tgtgaagagg | aatgtatgca | ttgcagtgga | gaaaactatg | acggcaaaat | ttccaagacc | 600 |
| atgtctggac | tggaatgcca | ggcctgggac | tctcagagcc | cacacgctca | tggatacatt | 660 |
| ccttccaaat | ttccaaacaa | gaacctgaag | aagaattact | gtcgtaaccc | cgatagggag | 720 |
| ctgcggcctt | ggtgtttcac | caccgacccc | aacaagcgct | gggaactttg | tgacatcccc | 780 |
| cgctgcacaa | cacctccacc | atcttctggt | cccacctacc | agtgtctgaa | gggaacaggt | 840 |
| gaaaactatc | gcgggaatgt | ggctgttacc | gtgtccgggc | acacctgtca | gcactggagt | 900 |
| gcacagaccc | ctcacacaca | taacaggaca | ccagaaaact | tcccctgcaa | aaatttggat | 960 |
| gaaaactact | gccgcaatcc | tgacggaaaa | agggcccat | ggtgccatac | aaccaacagc | 1020 |
| caagtgcggt | gggagtactg | taagataccg | tcctgtgact | cctccccagt | atccacggaa | 1080 |
| caattggctc | ccacagcacc | acctgagcta | acccctgtgg | tccaggactg | ctaccatggt | 1140 |
| gatggacaga | gctaccgagg | cacatcctcc | accaccacca | caggaaagaa | gtgtcagtct | 1200 |
| tggtcatcta | tgacaccaca | ccggcaccag | aagacccccag | aaaactaccc | aaatgctggc | 1260 |

-continued

```
ctgacaatga actactgcag gaatccagat gccgataaag gcccctggtg ttttaccaca      1320
gaccccagcg tcaggtggga gtactgcaac ctgaaaaaat gctcaggaac agaagcgagt      1380
gttgtagcac ctccgcctgt tgtcctgctt ccagatgtag agactccttc cgaagaagac      1440
tgtatgtttg ggaatgggaa aggataccga ggcaagaggg cgaccactgt tactgggacg      1500
ccatgccagg actgggctgc ccaggagccc atagacaca gcattttcac tccagagaca      1560
aatccacggg cggtctgga aaaaaattac tgccgtaacc ctgatggtga tgtaggtggt      1620
ccctggtgct acacgacaaa tccaagaaaa ctttacgact actgtgatgt ccctcagtgt      1680 gcggccccctt catttgattg tgggaagcct caagtggagc cgaagaaatg tcctggaagg      1740
gttgtagggg ggtgtgtggc ccacccacat tcctggccct ggcaagtcag tcttagaaca      1800
aggtttggaa tgcacttctg tggaggcacc ttgatatccc cagagtgggt gttgactgct      1860
gcccactgct tggagaagtc cccaaggcct tcatcctaca aggtcatcct gggtgcacac      1920
caagaagtga atctcgaacc gcatgttcag gaaatagaag tgtctaggct gttcttggag      1980
cccacacgaa aagatattgc cttgctaaag ctaagcagtc ctgccgtcat cactgacaaa      2040
gtaatcccag cttgtctgcc atccccaaat tatgtggtcg ctgaccggac cgaatgtttc      2100
atcactggct ggggagaaac ccaaggtact tttggagctg gccttctcaa ggaagcccag      2160
ctccctgtga ttgagaataa agtgtgcaat cgctatgagt ttctgaatgg aagagtccaa      2220
tccaccgaac tctgtgctgg gcatttggcc ggaggcactg acagttgcca gggtgacagt      2280
ggaggtcctc tggtttgctt cgagaaggac aaatacattt tacaaggagt cacttcttgg      2340
ggtcttggct gtgcacgccc caataagcct ggtgtctatg ttcgtgtttc aaggtttgtt      2400
acttggattg agggagtgat gagaaataat taa                                  2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen (from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
```

```
            145                 150                 155                 160
        Gly Pro Trp Cys Tyr Thr Thr Asp Pro Glu Lys Arg Tyr Asp Tyr Cys
                        165                 170                 175
        Asp Ile Leu Glu Cys Glu Glu Cys Met His Cys Ser Gly Glu Asn
                        180                 185                 190
        Tyr Asp Gly Lys Ile Ser Lys Thr Met Ser Gly Leu Glu Cys Gln Ala
                        195                 200                 205
        Trp Asp Ser Gln Ser Pro His Ala His Gly Tyr Ile Pro Ser Lys Phe
                    210                 215                 220
        Pro Asn Lys Asn Leu Lys Lys Asn Tyr Cys Arg Asn Pro Asp Arg Glu
        225                 230                 235                 240
        Leu Arg Pro Trp Cys Phe Thr Thr Asp Pro Asn Lys Arg Trp Glu Leu
                        245                 250                 255
        Cys Asp Ile Pro Arg Cys Thr Thr Pro Pro Ser Ser Gly Pro Thr
                        260                 265                 270
        Tyr Gln Cys Leu Lys Gly Thr Gly Glu Asn Tyr Arg Gly Asn Val Ala
                    275                 280                 285
        Val Thr Val Ser Gly His Thr Cys Gln His Trp Ser Ala Gln Thr Pro
                290                 295                 300
        His Thr His Asn Arg Thr Pro Glu Asn Phe Pro Cys Lys Asn Leu Asp
        305                 310                 315                 320
        Glu Asn Tyr Cys Arg Asn Pro Asp Gly Lys Arg Ala Pro Trp Cys His
                        325                 330                 335
        Thr Thr Asn Ser Gln Val Arg Trp Glu Tyr Cys Lys Ile Pro Ser Cys
                    340                 345                 350
        Asp Ser Ser Pro Val Ser Thr Glu Gln Leu Ala Pro Thr Ala Pro Pro
                355                 360                 365
        Glu Leu Thr Pro Val Val Gln Asp Cys Tyr His Gly Asp Gly Gln Ser
            370                 375                 380
        Tyr Arg Gly Thr Ser Ser Thr Thr Thr Gly Lys Lys Cys Gln Ser
        385                 390                 395                 400
        Trp Ser Ser Met Thr Pro His Arg His Gln Lys Thr Pro Glu Asn Tyr
                        405                 410                 415
        Pro Asn Ala Gly Leu Thr Met Asn Tyr Cys Arg Asn Pro Asp Ala Asp
                    420                 425                 430
        Lys Gly Pro Trp Cys Phe Thr Thr Asp Pro Ser Val Arg Trp Glu Tyr
                    435                 440                 445
        Cys Asn Leu Lys Lys Cys Ser Gly Thr Glu Ala Ser Val Val Ala Pro
                    450                 455                 460
        Pro Pro Val Val Leu Leu Pro Asp Val Glu Thr Pro Ser Glu Glu Asp
        465                 470                 475                 480
        Cys Met Phe Gly Asn Gly Lys Gly Tyr Arg Gly Lys Arg Ala Thr Thr
                        485                 490                 495
        Val Thr Gly Thr Pro Cys Gln Asp Trp Ala Ala Gln Glu Pro His Arg
                    500                 505                 510
        His Ser Ile Phe Thr Pro Glu Thr Asn Pro Arg Ala Gly Leu Glu Lys
                    515                 520                 525
        Asn Tyr Cys Arg Asn Pro Asp Gly Asp Val Gly Gly Pro Trp Cys Tyr
                    530                 535                 540
        Thr Thr Asn Pro Arg Lys Leu Tyr Asp Tyr Cys Asp Val Pro Gln Cys
        545                 550                 555                 560
        Ala Ala Pro Ser Phe Asp Cys Gly Lys Pro Gln Val Glu Pro Lys Lys
                        565                 570                 575
```

```
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
            595                 600                 605
Gly Thr Leu Ile Ser Pro Glu Trp Val Leu Thr Ala Ala His Cys Leu
610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
            675                 680                 685
Pro Asn Tyr Val Val Ala Asp Arg Thr Glu Cys Phe Ile Thr Gly Trp
            690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
            755                 760                 765
Lys Asp Lys Tyr Ile Leu Gln Gly Val Thr Ser Trp Gly Leu Gly Cys
            770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga    120
ttctcacctg ctacacaccc ctcagaggga ctggaggaga actactgcag gaatccagac    180
aacgatccgc aggggccctg tgctatact  actgatccag aaaagagata tgactactgc    240
gacattcttg agtgtgaaga ggaatgtatg cattgcagtg agaaaacta  tgacggcaaa    300 atttccaaga ccatgtctgg actggaatgc caggcctggg actctcagag cccacacgct    360
catggataca ttccttccaa atttccaaac aagaacctga agaagaatta ctgtcgtaac    420
cccgataggg agctgcggcc ttggtgtttc accaccgacc ccaacaagcg ctgggaactt    480
tgtgacatcc ccgctgcac  aacacctcca ccatcttctg gtcccaccta ccagtgtctg    540
aagggaacag gtgaaaacta tcgcgggaat gtggctgtta ccgtgtccgg cacacctgt     600 cagcactgga gtgcacagac ccctcacaca cataacagga caccagaaaa cttcccctgc    660
```

```
aaaaatttgg atgaaaacta ctgccgcaat cctgacggaa aaagggcccc atggtgccat      720
acaaccaaca gccaagtgcg gtgggagtac tgtaagatac cgtcctgtga ctcctcccca      780
gtatccacgg aacaattggc tcccacagca ccacctgagc taaccctgt ggtccaggac       840 tgctaccatg gtgatggaca gagctaccga ggcacatcct ccaccaccac acaggaaag       900 aagtgtcagt cttggtcatc tatgacacca caccggcacc agaagacccc agaaaactac      960
ccaaatgctg gcctgacaat gaactactgc aggaatccag atgccgataa aggcccctgg     1020
tgttttacca cagaccccag cgtcaggtgg gagtactgca acctgaaaaa atgctcagga     1080
acagaagcga gtgttgtagc acctccgcct gttgtcctgc ttccagatgt agagactcct     1140
tccgaagaag actgtatgtt tgggaatggg aaaggatacc gaggcaagag ggcgaccact     1200
gttactggga cgccatgcca ggactgggct gcccaggagc ccatagaca cagcattttc      1260 actccagaga caaatccacg ggcgggtctg gaaaaaaatt actgccgtaa ccctgatggt     1320
gatgtaggtg gtccctggtg ctacacgaca aatccaagaa aactttacga ctactgtgat     1380
gtccctcagt gtgcggcccc ttcatttgat tgtgggaagc tcaagtgga gccgaagaaa      1440 tgtcctggaa gggttgtagg ggggtgtgtg gcccacccac attcctggcc ctggcaagtc     1500
agtcttagaa caaggtttgg aatgcacttc tgtgaggca ccttgatatc cccagagtgg      1560
gtgttgactg ctgcccactg cttggagaag tccccaaggc cttcatccta caaggtcatc     1620
ctgggtgcac accaagaagt gaatctcgaa ccgcatgttc aggaaataga agtgtctagg     1680
ctgttcttgg agcccacacg aaaagatatt gccttgctaa agctaagcag tcctgccgtc     1740
atcactgaca aagtaatccc agcttgtctg ccatccccaa attatgtggt cgctgaccgg     1800
accgaatgtt tcatcactgg ctggggagaa acccaaggta cttttggagc tggccttctc     1860
aaggaagccc agctccctgt gattgagaat aaagtgtgca atcgctatga gtttctgaat     1920
ggaagagtcc aatccaccga actctgtgct gggcatttgg ccggaggcac tgacagttgc     1980
cagggtgaca gtggaggtcc tctggtttgc ttcgagaagg acaaatacat tttacaagga     2040
gtcacttctt ggggtcttgg ctgtgcacgc cccaataagc ctggtgtcta tgttcgtgtt     2100
tcaaggtttg ttacttggat tgagggagtg atgagaaata attaa                    2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-
      plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95
```

```
Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
        180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
        290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
        450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
```

```
                515                 520                 525
Glu Lys Ser Pro Arg Pro Ser Ser Tyr Lys Val Ile Leu Gly Ala His
        530                 535                 540
Gln Glu Val Asn Leu Glu Pro His Val Gln Glu Ile Glu Val Ser Arg
545                 550                 555                 560
Leu Phe Leu Glu Pro Thr Arg Lys Asp Ile Ala Leu Leu Lys Leu Ser
                565                 570                 575
Ser Pro Ala Val Ile Thr Asp Lys Val Ile Pro Ala Cys Leu Pro Ser
            580                 585                 590
Pro Asn Tyr Val Val Ala Asp Arg Thr Glu Cys Phe Ile Thr Gly Trp
                595                 600                 605
Gly Glu Thr Gln Gly Thr Phe Gly Ala Gly Leu Leu Lys Glu Ala Gln
        610                 615                 620
Leu Pro Val Ile Glu Asn Lys Val Cys Asn Arg Tyr Glu Phe Leu Asn
625                 630                 635                 640
Gly Arg Val Gln Ser Thr Glu Leu Cys Ala Gly His Leu Ala Gly Gly
                645                 650                 655
Thr Asp Ser Cys Gln Gly Asp Ser Gly Gly Pro Leu Val Cys Phe Glu
            660                 665                 670
Lys Asp Lys Tyr Ile Leu Gln Gly Val Thr Ser Trp Gly Leu Gly Cys
                675                 680                 685
Ala Arg Pro Asn Lys Pro Gly Val Tyr Val Arg Val Ser Arg Phe Val
        690                 695                 700
Thr Trp Ile Glu Gly Val Met Arg Asn Asn
705                 710
```

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-plasminogen)

<400> SEQUENCE: 7

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa agcaacaat gtgtgataat ggctgaaaac     180
aggaagtcct ccataatcat taggatgaga gatgtagttt atttgaaaaa gaaagtgtat     240
ctctcagagt gcaagactgg aatggaaag aactacagag gacgatgtc caaacaaaa     300 aatggcatca cctgtcaaaa atggagttcc acttctcccc acagacctag attctcacct     360
gctacacacc cctcagaggg actggaggag aactactgca ggaatccaga caacgatccg     420 cagggggccct ggtgctatac tactgatcca gaaagagat atgactactg cgacattctt     480
gagtgtgaag aggcggcccc ttcatttgat tgtgggaagc tcaagtgga gccgaagaaa     540 tgtcctggaa gggttgtagg ggggtgtgtg gcccaccac attcctggcc ctggcaagtc     600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaataga agtgtctagg     780
ctgttcttgg agcccacacg aaaagatatt gccttgctaa agctaagcag tcctgccgtc     840
atcactgaca aagtaatccc agcttgtctg ccatccccaa attatgtggt cgctgaccgg     900
```

```
accgaatgtt tcatcactgg ctggggagaa acccaaggta cttttggagc tggccttctc    960
aaggaagccc agctccctgt gattgagaat aaagtgtgca atcgctatga gtttctgaat   1020
ggaagagtcc aatccaccga actctgtgct gggcatttgg ccggaggcac tgacagttgc   1080
cagggtgaca gtggaggtcc tctggtttgc ttcgagaagg acaaatacat tttacaagga   1140
gtcacttctt ggggtcttgg ctgtgcacgc cccaataagc ctggtgtcta tgttcgtgtt   1200
tcaaggtttg ttacttggat tgagggagtg atgagaaata attaa                   1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

```
Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300
```

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-
      plasminogen)

<400> SEQUENCE: 9

| | | | | | |
|---|---|---|---|---|---|
| gtcaggtggg | agtactgcaa | cctgaaaaaa | tgctcaggaa | cagaagcgag | tgttgtagca | 60 |
| cctccgcctg | ttgtcctgct | tccagatgta | gagactcctt | ccgaagaaga | ctgtatgttt | 120 |
| gggaatggga | aaggataccg | aggcaagagg | gcgaccactg | ttactgggac | gccatgccag | 180 |
| gactgggctg | cccaggagcc | ccatagacac | agcattttca | ctccagagac | aaatccacgg | 240 |
| gcgggtctgg | aaaaaaatta | ctgccgtaac | cctgatggtg | atgtaggtgg | tccctggtgc | 300 |
| tacacgacaa | atccaagaaa | actttacgac | tactgtgatg | tccctcagtg | tgcggcccct | 360 |
| tcatttgatt | gtgggaagcc | tcaagtggag | ccgaagaaat | gtcctggaag | ggttgtaggg | 420 |
| gggtgtgtgg | cccacccaca | ttcctggccc | tggcaagtca | gtcttagaac | aaggtttgga | 480 |
| atgcacttct | gtggaggcac | cttgatatcc | ccagagtggg | tgttgactgc | tgcccactgc | 540 |
| ttggagaagt | ccccaaggcc | ttcatcctac | aaggtcatcc | tgggtgcaca | ccaagaagtg | 600 |
| aatctcgaac | cgcatgttca | ggaaatagaa | gtgtctaggc | tgttcttgga | gcccacacga | 660 |
| aaagatattg | ccttgctaaa | gctaagcagt | cctgccgtca | tcactgacaa | agtaatccca | 720 |
| gcttgtctgc | catccccaaa | ttatgtggtc | gctgaccgga | ccgaatgttt | catcactggc | 780 |
| tggggagaaa | cccaaggtac | ttttggagct | ggccttctca | aggaagccca | gctccctgtg | 840 |
| attgagaata | aagtgtgcaa | tcgctatgag | tttctgaatg | gaagagtcca | atccaccgaa | 900 |
| ctctgtgctg | gcatttggc | cggaggcact | gacagttgcc | agggtgacag | tggaggtcct | 960 |
| ctggtttgct | tcgagaagga | caaatacatt | ttacaaggag | tcacttcttg | gggtcttggc | 1020 |
| tgtgcacgcc | ccaataagcc | tggtgtctat | gttcgtgttt | caaggtttgt | tacttggatt | 1080 |
| gagggagtga | tgagaaataa | ttaa | | | | 1104 |

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-
      plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
            115                 120                 125

Val Glu Pro Lys Lys Cys Pro Gly Arg Val Val Gly Gly Cys Val Ala
        130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
    210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365
```

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-

<400> SEQUENCE: 11

```
gcccttcat tgattgtgg gaagcctcaa gtggagccga agaaatgtcc tggaagggtt      60
gtaggggggt gtgtggccca cccacattcc tggccctggc aagtcagtct tagaacaagg    120
tttggaatgc acttctgtgg aggcaccttg atatcccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750
```

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-plasminogen)

<400> SEQUENCE: 12

```
Ala Pro Ser Phe Asp Cys Gly Lys Pro Gln Val Glu Pro Lys Lys Cys
1               5                   10                  15
Pro Gly Arg Val Val Gly Gly Cys Val Ala His Pro His Ser Trp Pro
            20                  25                  30
Trp Gln Val Ser Leu Arg Thr Arg Phe Gly Met His Phe Cys Gly Gly
        35                  40                  45
Thr Leu Ile Ser Pro Glu Trp Val Leu Thr Ala Ala His Cys Leu Glu
    50                  55                  60
Lys Ser Pro Arg Pro Ser Ser Tyr Lys Val Ile Leu Gly Ala His Gln
65                  70                  75                  80
Glu Val Asn Leu Glu Pro His Val Gln Glu Ile Glu Val Ser Arg Leu
                85                  90                  95
Phe Leu Glu Pro Thr Arg Lys Asp Ile Ala Leu Leu Lys Leu Ser Ser
            100                 105                 110
Pro Ala Val Ile Thr Asp Lys Val Ile Pro Ala Cys Leu Pro Ser Pro
        115                 120                 125
Asn Tyr Val Val Ala Asp Arg Thr Glu Cys Phe Ile Thr Gly Trp Gly
    130                 135                 140
Glu Thr Gln Gly Thr Phe Gly Ala Gly Leu Leu Lys Glu Ala Gln Leu
145                 150                 155                 160
Pro Val Ile Glu Asn Lys Val Cys Asn Arg Tyr Glu Phe Leu Asn Gly
                165                 170                 175
Arg Val Gln Ser Thr Glu Leu Cys Ala Gly His Leu Ala Gly Gly Thr
            180                 185                 190
Asp Ser Cys Gln Gly Asp Ser Gly Gly Pro Leu Val Cys Phe Glu Lys
        195                 200                 205
```

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13
gttgtagggg ggtgtgtggc ccacccacat tcctggccct gcaagtcag tcttagaaca      60
aggtttggaa tgcacttctg tggaggcacc ttgatatccc cagagtgggt gttgactgct    120
gcccactgct tggagaagtc cccaaggcct tcatcctaca aggtcatcct gggtgcacac    180
caagaagtga atctcgaacc gcatgttcag gaaatagaag tgtctaggct gttcttggag    240
cccacacgaa aagatattgc cttgctaaag ctaagcagtc ctgccgtcat cactgacaaa    300
gtaatcccag cttgtctgcc atccccaaat tatgtggtcg ctgaccggac cgaatgtttc    360
atcactggct ggggagaaac ccaaggtact tttggagctg ccttctcaa ggaagcccag    420
ctccctgtga ttgagaataa agtgtgcaat cgctatgagt ttctgaatgg aagagtccaa    480
tccaccgaac tctgtgctgg gcatttggcc ggaggcactg acagttgcca gggtgacagt    540
ggaggtcctc tggtttgctt cgagaaggac aaatacattt tacaaggagt cacttcttgg    600
ggtcttggct gtgcacgccc caataagcct ggtgtctatg ttcgtgtttc aaggtttgtt    660
acttggattg agggagtgat gaga                                            684

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
      protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

```
Gly Thr Phe Gly Ala Gly Leu Leu Lys Glu Ala Gln Leu Pro Val Ile
    130             135             140

Glu Asn Lys Val Cys Asn Arg Tyr Glu Phe Leu Asn Gly Arg Val Gln
145             150             155                     160

Ser Thr Glu Leu Cys Ala Gly His Leu Ala Gly Gly Thr Asp Ser Cys
            165             170                 175

Gln Gly Asp Ser Gly Gly Pro Leu Val Cys Phe Glu Lys Asp Lys Tyr
        180             185                 190

Ile Leu Gln Gly Val Thr Ser Trp Gly Leu Gly Cys Ala Arg Pro Asn
        195             200             205

Lys Pro Gly Val Tyr Val Arg Val Ser Arg Phe Val Thr Trp Ile Glu
    210             215             220

Gly Val Met Arg
225
```